(12) United States Patent
Reiffenrath et al.

(10) Patent No.: US 6,444,279 B1
(45) Date of Patent: Sep. 3, 2002

(54) LIQUID CRYSTAL PROPENE OR PROPENYL NITRILE DERIVATIVES

(75) Inventors: Volker Reiffenrath, Rossdorf; Harald Hirschmann, Darmstadt, both of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/463,314

(22) PCT Filed: Jul. 14, 1998

(86) PCT No.: PCT/EP98/04366
§ 371 (c)(1),
(2), (4) Date: Jan. 24, 2000

(87) PCT Pub. No.: WO99/05097
PCT Pub. Date: Feb. 4, 1999

(30) Foreign Application Priority Data

Jul. 24, 1997 (DE) .......................... 197 31 906
Sep. 29, 1997 (DE) .......................... 197 42 898

(51) Int. Cl.$^7$ .................. C09K 19/34; C09K 19/30; C09K 19/20; C07C 255/07; C07D 239/02; C07D 319/06; C07D 213/06

(52) U.S. Cl. .............. 428/1.1; 252/299.61; 252/299.62; 252/299.63; 252/299.66; 544/242; 544/335; 546/350; 549/369; 558/401

(58) Field of Search ................. 252/299.61, 299.62, 252/299.63, 299.64, 299.65, 299.66, 299.67; 428/1.1; 544/242, 335; 546/184, 350; 549/369; 558/401

(56) References Cited

U.S. PATENT DOCUMENTS 6,017,467 A * 1/2000 Fujita et al. ........... 252/299.01

FOREIGN PATENT DOCUMENTS

| EP | 0310676 | 4/1989 |
| EP | 0816332 | 1/1998 |
| GB | 2111992 | 7/1983 |

OTHER PUBLICATIONS

Chemical Abstracts, vol. 102 No. 25, Jun. 24, 1985; Abstract No. 220593"phenylpropiolnitrile derivatives &JP 60 019756.

Chemical Abstracts,vol. 104, No. 18, May 5, 1986; Abstract No. 160058"propynenitrile derivatives & JP 60 169455.

Chemical Abstracts, vol.104, No. 14, Apr. 7, 1986; Abstract No. 120516"Propynenitrile derivatives for liquid crystal compositions & JP 60 188358.

Chemical Abstracts, vol. 102 No. 1, Jan. 7, 1985; Abstract No. 005964"4–acyloxyphenylpropionitriles &JP 59 139353.

Chemical Abstracts, vol. 097, No. 9, Aug. 30, 1982; Abstract No. 072113"Cinnamonitriles &JP 57 070851.

Chemical Abstracts, vol. 093, No. 13, Sep. 29, 1980; Abstract No. 132157"Cyclohexylcinnimonitriles &JP 55 009012.

Chemical Abstract, vol. 102, No. 19, May 13, 1985, Abstract No. 166483"4–Pentylbiphenyl–4'–propionitrile & JP 59 190958.

Chemical Abstracts, vol. 097, No. 11, Sep. 13, 1982, Abstract No. 091973 "Cinnamonitriles" &JP 57 035552.

Chemical Abstracts, vol. 093, No. 9, Sep. 1, 1980, Abstract No. 095021 & JP 55 011529.

* cited by examiner

*Primary Examiner*—Shean C. Wu
(74) *Attorney, Agent, or Firm*—Millen, White, Zelano & Branigan, P.C.

(57) ABSTRACT

Acetylene derivatives of the formula I

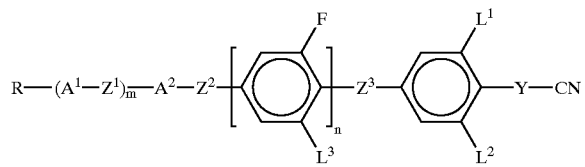

in which

R, $A^1$, $A^2$, $Z^1$, $Z^2$, $Z^3$, $L^1$, $L^2$, $L^3$, Y, m and n are as defined herein are suitable as components of liquid-crystalline media.

16 Claims, No Drawings

LIQUID CRYSTAL PROPENE OR PROPENYL NITRILE DERIVATIVES

The present invention relates to acetylene derivatives of the formula I

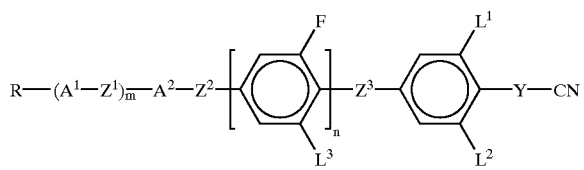

in which
R is an alkyl or alkenyl radical having 1 to 15 carbon atoms which is unsubstituted, mono-substituted by CN or $CF_3$ so at least monosubstituted by halogen, where, in addition, one or more —$CH_2$— groups in these radicals may be replaced, in each case independently of one another, by —O—, —S—,

—CO—, —CO—O—, —O—CO— or —O—CO—O— in such a way that O atoms are not linked directly to one another,
$A^1$ and $A^2$ are each, independently of one another,
(a) a trans-1,4-cyclohexylene radical, in which, in addition, one or more non-adjacent —$CH_2$— groups may be replaced by —O— and/or —S—,
(b) a 1,4-phenylene radical, in which, in addition, one so two CH groups may be replaced by N,
(c) trans-1,4-cyclohexenylene,
(d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene-2,6-diyl,
where the radicals (a) to (c) may be monosubstituted or disubstituted by fluorine or $CH_3$,
$Z^1$, $Z^2$
and $Z^3$ are each, independently of one another, —CO—O—, —O—CO—, —$CH_2$O—, —O$CH_2$—, —$CH_2CH_2$—, —CH=CH—, —C≡C—, —$(CH_2)_4$—, —$OCF_2$—, —$CF_2$O—, —CH=CH—$CH_2CH_2$— or a single bond,
m is 0, 1 or 2,
n is 0 or 1,
$L^1$, $L^2$
and $L^3$ are each, independently of one another, H or F, and
Y is —C≡C—, —CH=CH—, —CF=CH—, —CH=CF— or —CF=CF—,
with the proviso that, in the case where
Y=—C≡C— or —CH=CH—,
a) n=1 and $Z^3$ is a single bond
or
b) $L^1$ and/or $L^2$ is/are fluorine
or
c) R is alkenyl or alkenyloxy having 2 to 12 carbon atoms
or
d) $A^2$ is a pyridine radical, a pyrimidine radical or a trans-1,4-cyclohexylene radical which is monosubstituted or disubstituted by fluorine or $CH_3$ or
e) one of the radicals $Z^1$, $Z^2$ or $Z^3$ is —CO—O—.

The invention furthermore relates to the use of these compounds as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases or the effect of dynamic scattering.

The invention has the object of finding novel, stable, liquid-crystalline or mesogenic compounds which are suitable as components of liquid-crystalline media and in particular simultaneously have comparatively low viscosity and relatively high dielectric anisotropy.

It has now been found that compounds of the formula I are eminently suitable as components of liquid-crystalline media. In particular, they have high $\Delta\varepsilon$ values at the same time as high clearing points. They can be used to obtain stable liquid-crystalline media having a broad mesophase range and advantageous optical and dielectric anisotropy values. These media furthermore have very good low-temperature behaviour.

Compounds of the formula

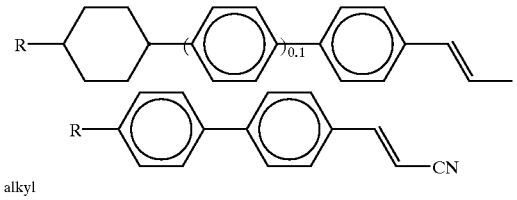

R = alkyl are disclosed, for example, in JP 55-149371, JP 55-009012, JP 55-011529, PL 137 995 and PL 138 286.

Cyanoethyne derivatives of the formula

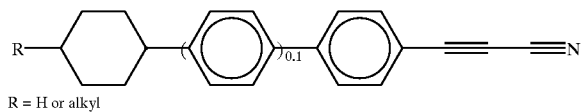

R = H or alkyl are disclosed in JP 59-190 958 A2, JP 60-169 455 A2, JP 60-188 358 A2 and JP 60-019 756 A2.

Biphenylacetylenes of the formula

R = alkyl are described in DE 32 46 440 A1.

However, the fluorinated compounds according to the invention are not mentioned therein.

However, in view of the extremely wide variety of areas of application of such compounds of high $\Delta\varepsilon$, it was desirable to have available further compounds of high nematogeneity which have properties which are precisely customized to the particular applications.

In addition, the provision of compounds of the formula I very generally considerably broadens the range of liquid-crystalline substances which are suitable, from various applicational points of view, for the preparation of liquid-crystalline mixtures.

The compounds of the formula I have a broad range of applications. Depending on the choice of substituents, these compounds can be used as base materials of which liquid-crystalline media are predominantly composed; however, compounds of the formula I can also be added to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and generally form liquid-crystalline mesophases in a temperature range which is favourably located for electro-optical use. The compounds according to the invention are stable chemically and thermally.

The invention thus relates to the compounds of the formula I and to the use of these compounds as components of liquid-crystalline media. The invention furthermore relates to liquid-crystalline media comprising at least one compound of the formula I, and. to liquid-crystal display elements, in particular electro-optical display elements, which contain media of this type.

For reasons of simplicity, $A^4$ and $A^3$ below denote a radical of the formula

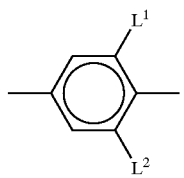

and

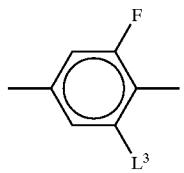

respectively, Cyc denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe may be unsubstituted or monosubstituted or disubstituted by F or CN.

$A^1$ and $A^2$ are preferably selected from the group consisting of Cyc, Che, Phe, Pyr, Pyd and Dio.

Accordingly, the compounds of the formula I include bicyclic compounds of the sub-formulae Ia and Ib:

| R-$A^2$-$A^4$-Y-CN | Ia |
| R-$A^2$-$Z^2$$A^4$-Y-CN | Ib | tricyclic compounds of the sub-formulae Ic to Ig

| R-$A^1$-$A^2$-$A^4$-Y-CN | Ic |
| R-$A^1$-$Z^1$-$A^2$-$A^4$-Y-CN | Id |
| R-$A^1$-$A^2$-$Z^2$-$A^4$-Y-CN | Ie |
| R-$A^1$-$A^2$-$A^4$-Y-CN | If |
| R-$A^1$-$Z^1$-$A^3$-$A^4$-Y-CN | Ig | and tetracyclic compounds of the sub-formulae Ih to Ik:

| R-$A^1$-$A^2$-$A^3$-$A^4$-Y-CN | Ih |
| R-$A^1$-$Z^1$-$A^2$-$A^3$-$A^4$-Y-CN | Ii |
| R-$A^1$-$A^2$-$Z^2$-$A^3$-$A^4$-Y-CN | Ij |
| R-$A^1$-$Z^1$-$A^2$-$Z^2$-$A^3$-$A^4$-Y-CN | Ik |

Y is preferably —C≡C—, furthermore —CF=CF— or —CF=CH—. Preference is also given to compounds of the formula I and of all sub-formulae in which $A^1$, $A^2$, $A^3$ and/or $A^4$ are 1,4-phenylene which is monosubstituted or disubstituted by F. In particular, these are 2-fluoro-1,4-phenylene, 3-fluoro-1,4-phenylene and 3,5-difluoro-1,4-phenylene.

$A^1$ and $A^2$ are preferably

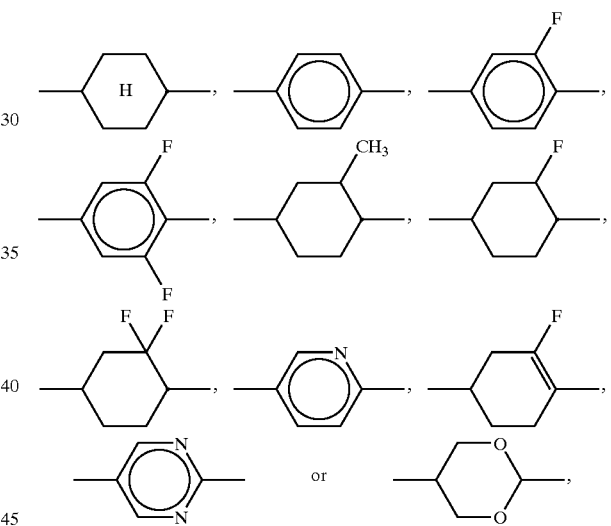

$Z^1$, $Z^2$ and $Z^3$ are preferably a single bond, —CO—O—, —O—CO— or —CH$_2$CH$_2$—, secondarily preferably —CF$_2$O—, —OCF$_2$—, —CH$_2$O— or —OCH$_2$—. If one of the radicals $Z^1$, $Z^2$ and $Z^3$ is —(CH$_2$)$_4$— or —CH=CH—CH$_2$CH$_2$—, the other radical $Z^1$ or $Z^2$ or $Z^3$ (if present) is preferably a single bond.

m and n are preferably 1 or 0, particular preference being given to compounds in which m=n=0, furthermore those in which m+n=1.

If R is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R is an alkyl radical in which one —CH$_2$— group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If R is an alkyl radical in which one —CH$_2$— group has been replaced by —O— and one has been replaced by —CO—, these are preferably adjacent. These thus contain, an acyloxy group —CO—C— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkyl radical in which one —CH$_2$— group has been replaced by unsubstituted or substituted —CH=CH— and an adjacent —CH$_2$— group has been replaced by —CO— or —CO—O— or —O—CO—, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If R is an alkyl or alkenyl radical which is monosubstituted by CN or CF$_3$, this radical is preferably straight-chain, and the substitution by CN or CF$_3$ is in the ω-position.

If R is an alkyl or alkenyl radical which is at least monosubstituted by halogen, this radical is preferably straight-chain, and halogen is preferably F or Cl. In the case of polysubstitution, halogen is preferably F. The resulting radicals also include perfluorinated radicals. In the case of monosubstitution, the fluorine or chlorine substituent can be in any desired position, but is preferably in the ω-position.

Compounds of the formula I which have wing groups R which are suitable for polymerization reactions are suitable for the preparation of liquid-crystalline polymers.

Compounds of the formula I containing branched wing groups R may occasionally be of importance owing to. better solubility in the customary liquid-crystalline base materials, but in particular as chiral dopants if they are optically active. Smectic compounds of this type are suitable as components of ferroelectric materials.

Compounds of the formula I having SA phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If R is an alkyl radical in which two or more —CH$_2$— groups have been replaced by —O— and/or —CO—O—, this can be straight-chain or branched. It is preferably branched and has 3 to 12 carbon atoms. Accordingly,, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-bis-carboxydecyl, bis(methoxycarbonyl)methyl, 2,2-bis-(methoxycarbonyl)ethyl, 3,3-bis(methoxycarbonyl)propyl, 4,4-bis(methoxycarbonyl) butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)-octyl, bis(ethoxycarbonyl)methyl, 2,2-bis(ethoxycarbonyl)-ethyl, 3,3-bis (ethoxycarbonyl)propyl, 4,4-bis (ethoxycarbonyl)-butyl or 5,5-bis(ethoxycarbonyl)hexyl.

Compounds of the formula I which have wing groups R which are suitable for polycondensation reactions are suitable for the preparation of liquid-crystalline. polycondensates.

The formula I covers the racemates of these compounds and the optical antipodes, and mixtures thereof.

Of the compounds of the formula I and of the sub-formulae, preference is given to those in which at least one of the radicals present therein has one of the preferred meanings indicated.

In the compounds of the formula I, preference is given to those stereoisomers in which the Cyc and piperidine rings are trans-1,4-disubstituted. Those of the abovementioned formulae which contain one or more Pyd, Pyr and/or Dio groups in each case include the two 2,5-positional isomers.

Preferred smaller groups of compounds are those of the sub-formulae I1 to I37:

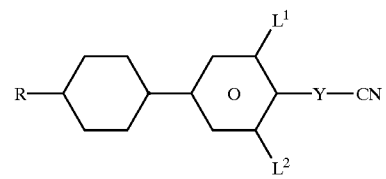

I1

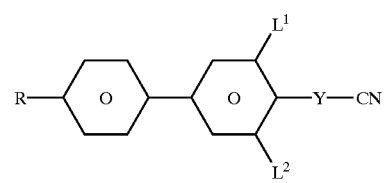

I2

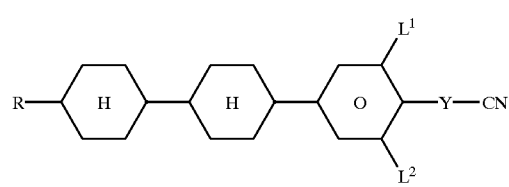

I3

I4
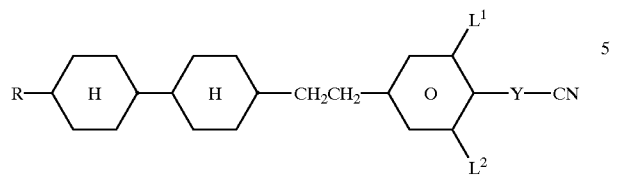
I5
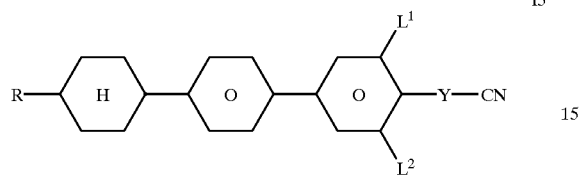
I6
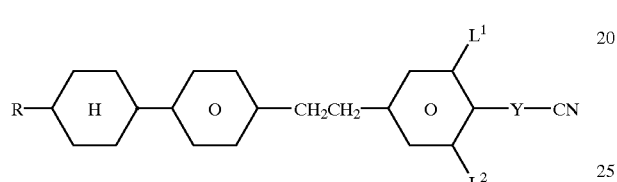
I7
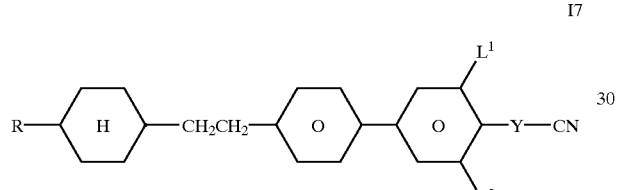
I8
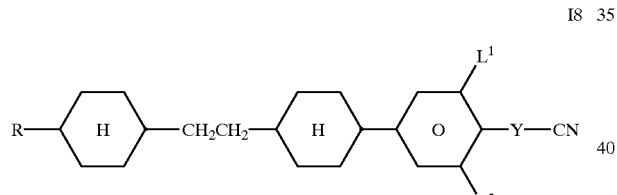
I9
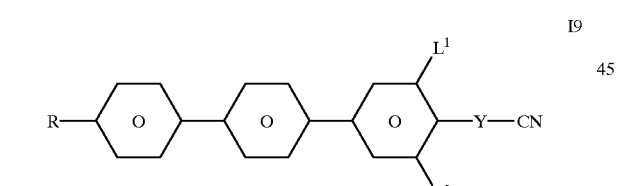
I10
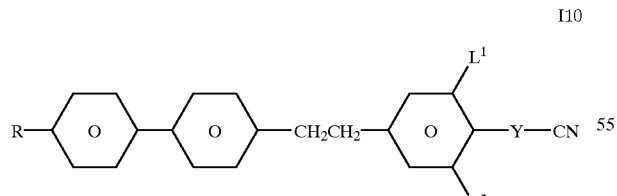
I11
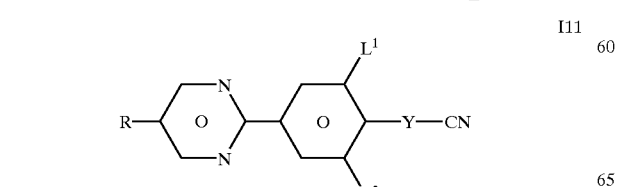
I12
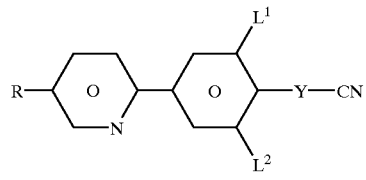
I13
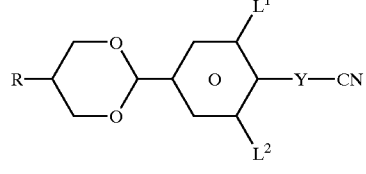
I14
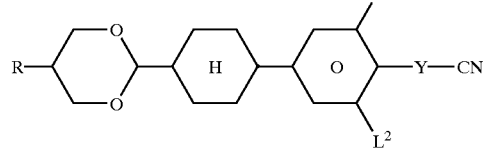
I15
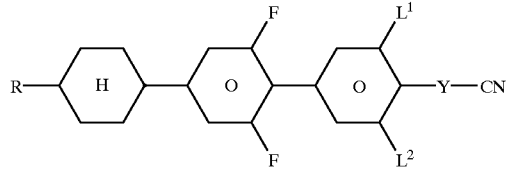
I16
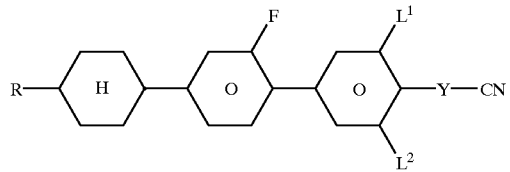
I17
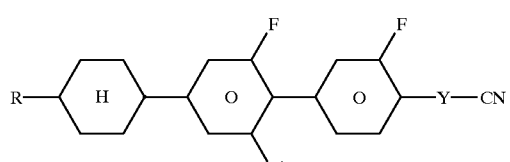
I18
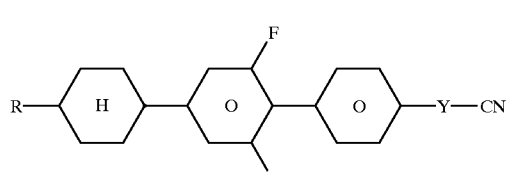
I19
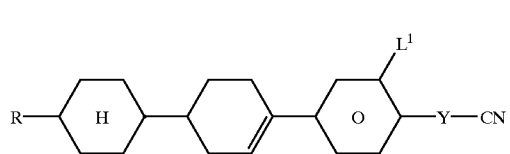

-continued

11

-continued

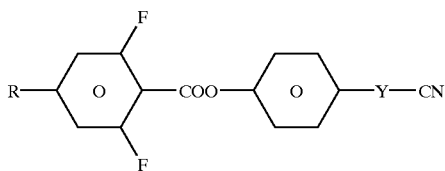
I37

Particularly preferred compounds are those of the sub-formulae I1, I2, I3, I4, I5, I8, I11, I13, I16, I21, I30, I31, I33, I34, I35, I36 and I37.

In the sub-formulae I1-I37, Y is preferably —C≡C— or —CF=CF—, furthermore —CF=CH—. R is preferably straight-chain alkyl, alkoxy, 1-E- or 3-E-alkenyl having up to 6 carbon atoms, furthermore 2-Z-alkenyl, 4-alkenyl or alkenyloxy.

For the purposes of the present invention, the term "1-E-alkenyl" covers radicals such as vinyl, 1-E-propenyl, 1-E-butenyl, 1-E-pentenyl, 1-E-hexenyl, 1-E-heptenyl, 1-E-octenyl, 1-E-nonenyl and 1-E-decenyl. The term "2-Z-alkenyl" covers radicals such as allyl, 2-Z-butenyl, 2-Z-pentenyl, 2-Z-hexenyl, 2-Z-heptenyl, 2-Z-octenyl, 2-Z-nonenyl and 2-Z-decenyl. The term "3-E-alkenyl" covers radicals such as 3-E-butenyl, 3-E-pentenyl, 3-E-hexenyl, 3-E-heptenyl, 3-E-octenyl, 3-E-nonenyl and 3-E-decenyl. The term "4-alkenyl" covers radicals such as 4-pentenyl and the E- and/or Z- form of 3-hexenyl, 4-heptenyl, 4-octenyl, 4-nonenyl and 4-decenyl.

The term "alkenyloxy" denotes alkenyloxy groups in which the oxygen is directly linked to a saturated carbon atom (i.e. groups having one or more carbon atoms between the double bond and the oxygen atom), such as (2-E-alkenyl)oxy, (3-alkenyl)oxy, (4-alkenyl)oxy, (5-alkenyl)oxy and the like. The term "(2-E-alkenyl)oxy" here covers radicals such as allyloxy, (2-E-butenyl)oxy, (2-E-pentenyl)oxy, (2-E-hexenyl) oxy, (2-E-heptenyl)oxy, (2-E-octenyl)oxy, (2-E-nonenyl)oxy and (2-E-decenyl)oxy. The term "(3-alkenyl) oxy" covers radicals such as (3-butenyl)oxy and the E- and/or Z-form of (3-pentenyl)oxy, (3-hexenyl)oxy, (3-hepentyl)oxy, (3-octenyl)oxy, (3-nonenyl)oxy and (3-decenyl)oxy. The term "(4-alkenyl)oxy" covers radicals such as (4-pentyl)oxy and the E- and/or Z- form of (4-hexenyl)oxy, (4-heptenyl)oxy, (4-octenyl)oxy, (4-nonenyl)oxy and (4-decenyl)oxy. The term "(5-alkenyl) oxy" covers radicals such as (5-hexenyl)oxy and the E- and/or Z-form of (5-heptenyl)oxy, (5-octenyl)oxy, (5-nonenyl)oxy and (5-decenyl)oxy.

It is self-evident to the person skilled in the art that claim 1 likewise covers all compounds of the formula I in which the H, N, O, C and F atoms have been replaced by their isotopes.

The 1,4-cyclohexenylene group preferably has the following structures:

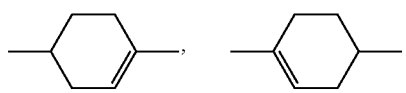

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and are suitable for said reactions.

12

Use can also be made here of variants which are known per se, but are not mentioned here in greater detail.

Scheme 1

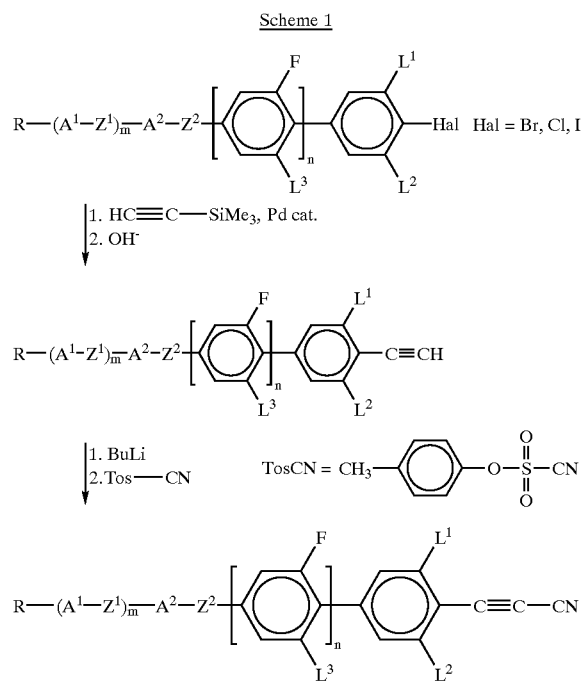

Scheme 2

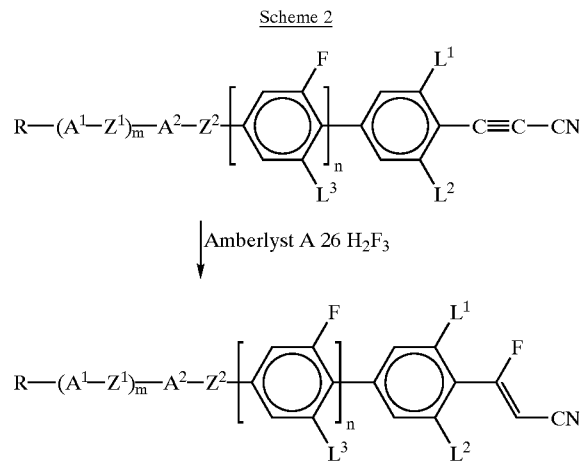

Scheme 3

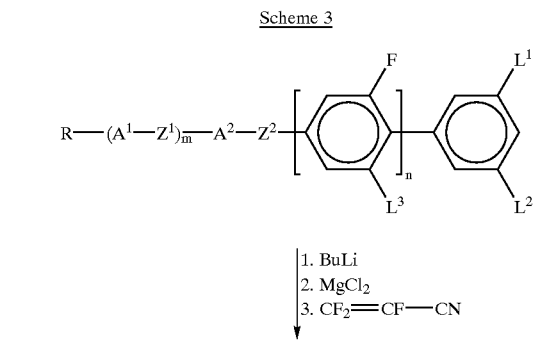

-continued
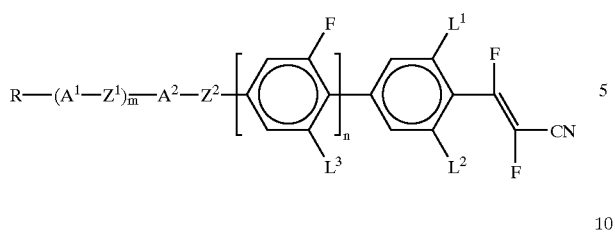
Scheme 4
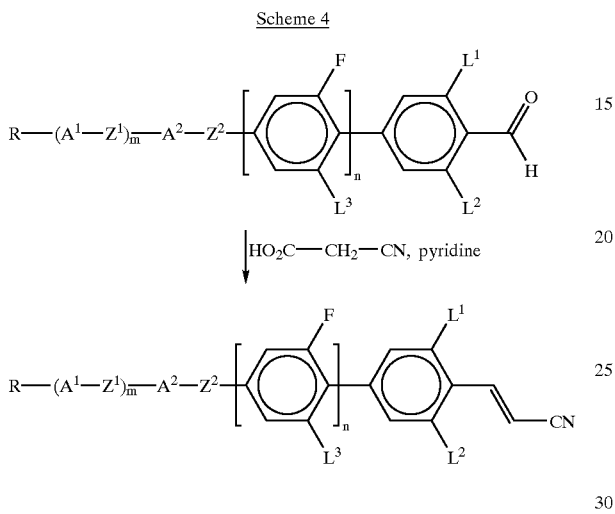
Preferred compounds are prepared, for example, as follows:
Scheme 5
Scheme 6
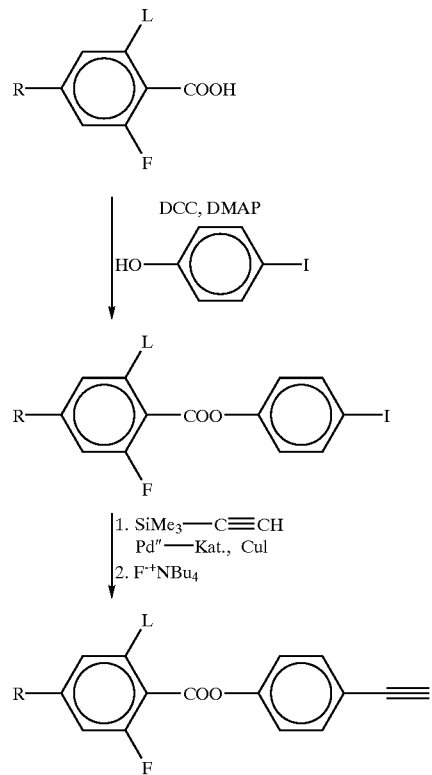
L = H, or F
Scheme 7
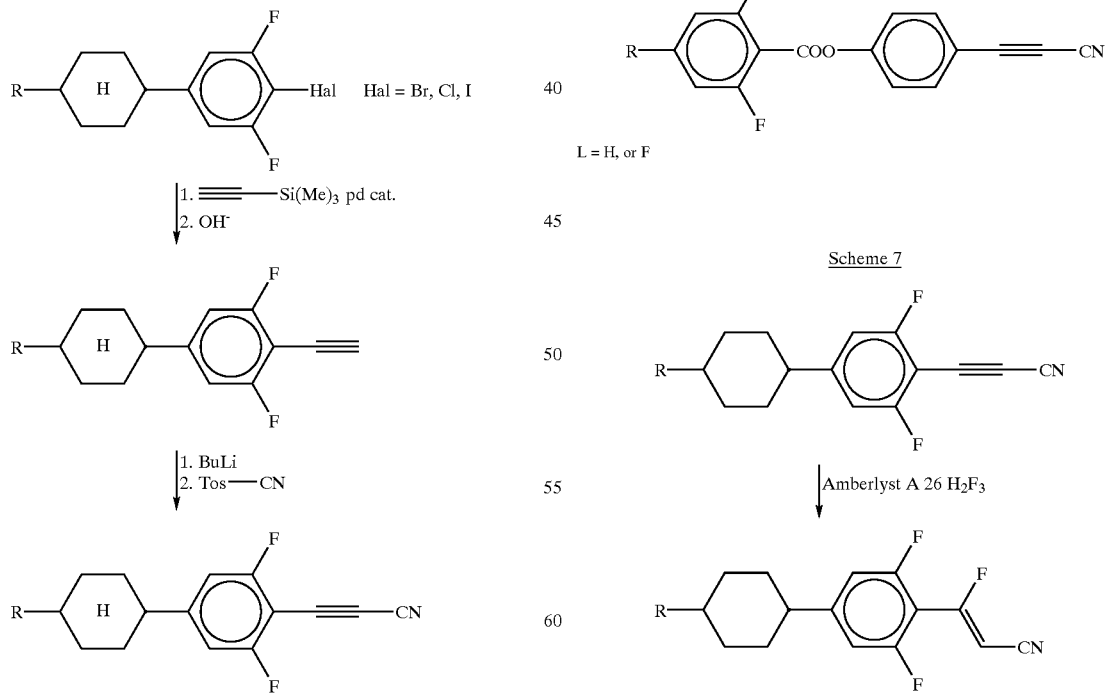

Scheme 8

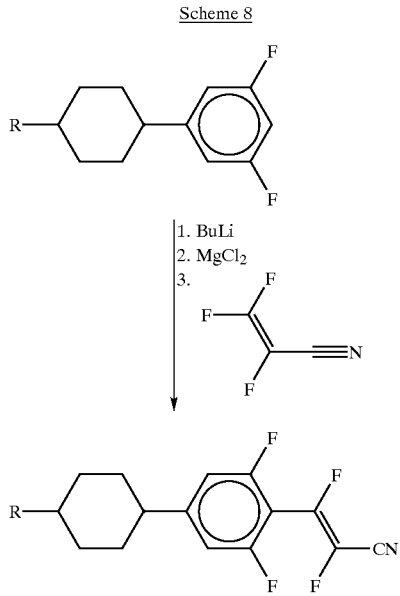

Scheme 9

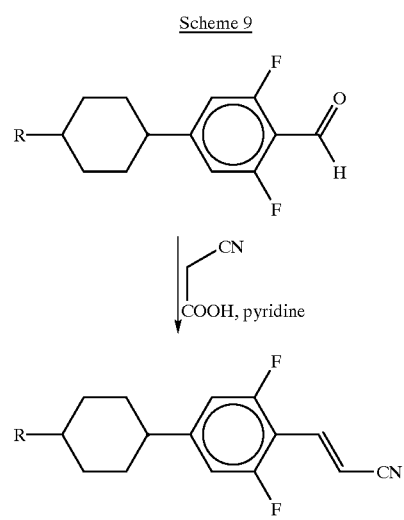

Scheme 10

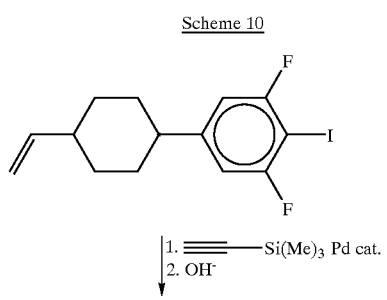

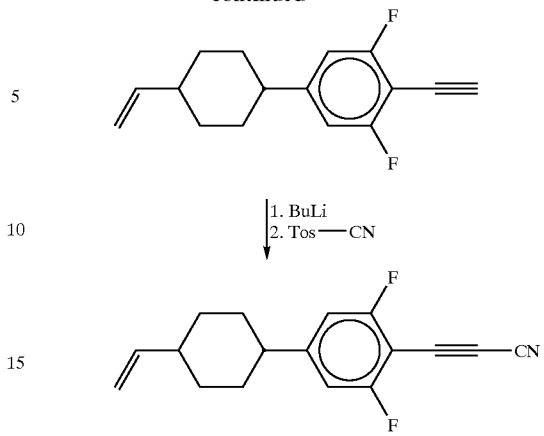

The liquid-crystalline media according to the invention preferably comprise from 2 to 40 components, in particular from 4 to 30 components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, 1,4-cyclobexenylene, preferably trans-1,4cyclobexylene. Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is known as group B, R" is —F, —Cl, —NCS or —(O)$_i$CH$_{3-(k+1)}$F$_k$Cl$_1$, where i is 0 or 1, and k+1 is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' is as defined for the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invent;on are preferably Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being from 5 to 90% and in particular from 10 to 90%.

The media according to the invention preferably comprise from 1 to 40%, particularly preferably from 5 to 30%, of compounds according to the invention. Further preferred media are those which comprise more than 40%, in particular from 45 to 90%, of compounds according to the invention. The media preferably comprise three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in such a manner that they can be used in all types of liquid-crystal display elements which have been disclosed hitherto. Additives of this type are known to those skilled in the art and are described in detail in the literature (H. Kelker/R. Hatz, Handbook of Liquid Crystals, Verlag Chemie, Weinheim, 1980). For example, it is possible to add pleochroic dyes for the production of colored guest-host systems, or substances for the modification of the dielectric anisotropy, the viscosity and/or the orientation of the nematic phases.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n and m carbon atoms respectively. The coding in Table B is self-evident. In Table A, only the acronym for the parent structure is given. In individual cases, the acronym for the parent structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |

The invention likewise relates to liquid-crystalline mixtures comprising at least one component of the formula I and preferably at least one further component selected from Tables A and B.

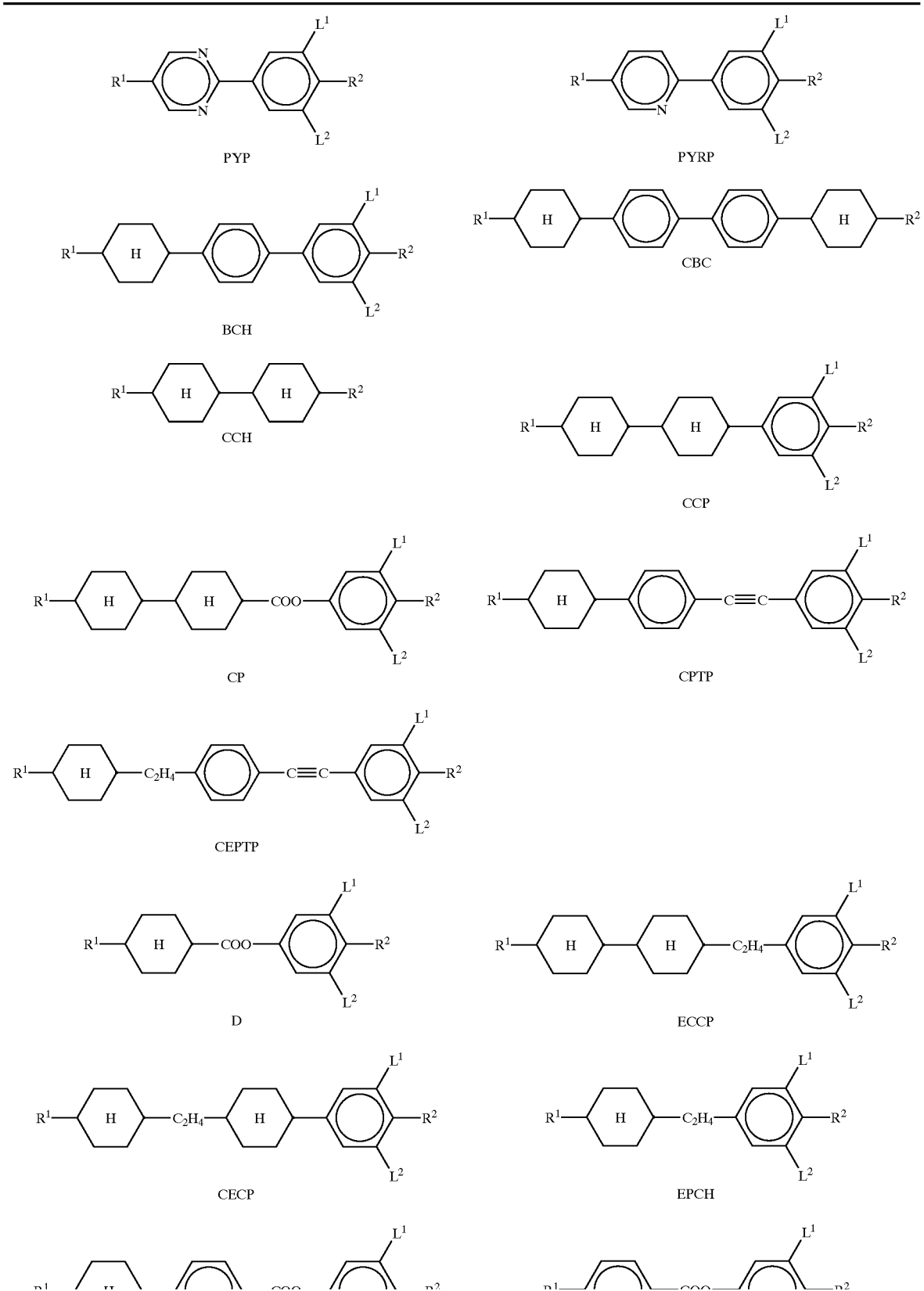

The examples below are intended to illustrate the invention without representing a limitation. Above and below, percentage data are per cent by weight. All temperatures are given in degrees Celsius. m.p. denotes melting point, c.p.=clearing point. Furthermore, C=crystalline state, N=nematic phase, S=smectic phase and I=isotropic phase. The numbers between these symbols indicate the conversion temperatures. Δn denotes optical anisotropy (589 nm, 20° C.), Δ∈ denotes the dielectric anisotropy [20° C., 1 kHz], and the flow viscosity (mm²/sec) was determined at 20° C.

"Conventional work-up" means that water is added if necessary, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

| | |
|---|---|
| DAST | diethylaminosulphur trifluoride |
| DMEU | 1,3-dimethyl-2-imidazolidinone |
| POT | potassium tertiary-butoxide |
| THF | tetrahydrofuran |
| pTsOH | p-toluenesulfonic acid |

EXAMPLE 1

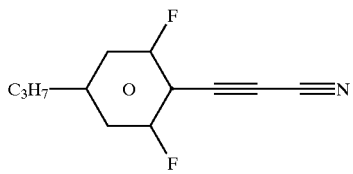

Step 1.1

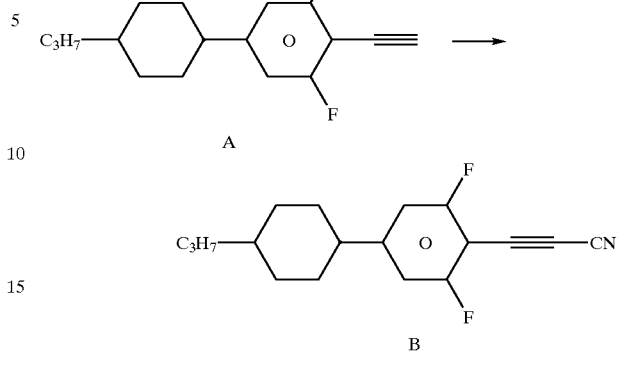

Under a nitrogen atmosphere, 0.019 mol of A are added with stirring to 30 ml of abs. THF. 0.021 mol of BuLi (15% solution in n-hexane) is added dropwise to the mixture at −65° C., and the mixture is then stirred for 0.5 h. After 0.021 mol of p-toluenesulfonyl cyanide in 10 ml of THF has been added at −60° C., the mixture is allowed to warm to 5° C. After hydrolysis, the solution is subjected to customary work-up. The crude product is recrystallized from ethanol and n-heptane. C 68 N (61.3) I; Δ∈=42.25; Δn=+0.208

The following compounds of the formula $$R-(A^1-Z^1)_{\overline{m}}-A^2-Z^2-\underset{L^2}{\overset{L^1}{\bigcirc}}-\equiv-\equiv N$$

are prepared analogously.

| R | —(A¹—Z¹)ₘ—A²—Z²— | L¹ | L² | |
|---|---|---|---|---|
| C₂H₅ | ⬡ | F | H | C 39 N 46.4 I; Δn = +0.202; Δε = 36.01 |
| C₂H₅ | ⬡ | F | F | C 45 I; Δn = 0.179; Δε = 40.45 |
| n-C₃H₇ | ⬡ | F | H | C 49 N 90.8 I; Δn = +0.225; Δε = 35.92 |
| n-C₄H₉ | ⬡ | F | H | C 18 N 91.3 I; Δn = +0.214; Δε = 33.59 |
| n-C₄H₉ | ⬡ | F | F | C 34 N 59.9 I; Δn = +0.182; Δε = 39.57 |
| n-C₅H₁₁ | ⬡ | F | H | C 35 N 101 I; Δn = +0.221; Δε = 32.94 |

-continued

| R | —(A¹—Z¹)ₘ—A²—Z²— | L¹ | L² | |
|---|---|---|---|---|
| n-C₅H₁₁ | cyclohexyl | F | F | C 53 N 72.5 I; Δn = +0.194; Δε = 38.6 |
| n-C₆H₁₃ | cyclohexyl | F | H | |
| n-C₆H₁₃ | cyclohexyl | F | F | |
| C₂H₅ | dicyclohexyl | F | F | C 96 N 268 I; Δn = +0.237; Δε = 37.02 |
| n-C₃H₇ | dicyclohexyl | F | F | |
| n-C₅H₁₁ | dicyclohexyl | F | F | |
| C₂H₅ | phenyl | F | H | |
| C₂H₅O | phenyl | F | H | |
| C₂H₅ | phenyl | F | F | |
| C₂H₅O | phenyl | F | F | |
| n-C₃H₇ | phenyl | F | H | |
| n-C₃H₇ | phenyl | F | F | C 75 N (51.0) I; Δn = +0.330; Δε = 51.48 |
| n-C₃H₇O | phenyl | F | F | |
| n-C₄H₉ | phenyl | F | H | |
| n-C₄H₉ | phenyl | F | F | |

-continued
| R | —(A¹—Z¹)ₘ—A²—Z²— | L¹ | L² | |
|---|---|---|---|---|
| n-C₅H₁₁ |  | F | H | |
| n-C₅H₁₁ |  | F | F | C 61 N(48.8) I; Δn = +0.320; Δε = 45.87 |
| C₂H₅ | 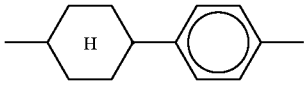 | F | H | |
| C₂H₅ | 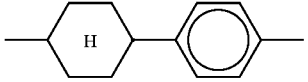 | F | F | |
| n-C₃H₇ | 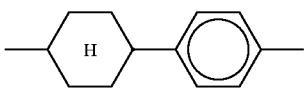 | F | H | |
| n-C₃H₇ | 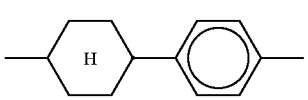 | F | F | |
| n-C₅H₁₁ | 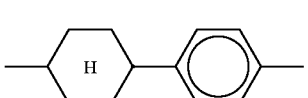 | F | H | |
| n-C₅H₁₁ |  | F | F | |
| n-C₆H₁₃ |  | F | H | |
| n-C₆H₁₃ |  | F | F | |
| C₂H₅ |  | F | H | |
| C₂H₅ | 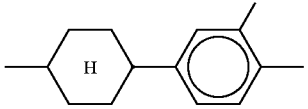 | F | F | |
| n-C₃H₇ |  | F | H | |

-continued

| R | —(A¹—Z¹)ₘ—A²—Z²— | L¹ | L² |
|---|---|---|---|
| n-C$_3$H$_7$ | Cy-Ph(F)- | F | F |
| n-C$_5$H$_{11}$ | Cy-Ph(F)- | F | H |
| n-C$_5$H$_{11}$ | Cy-Ph(F)- | F | F |
| n-C$_6$H$_{13}$ | Cy-Ph(F)- | F | H |
| n-C$_6$H$_{13}$ | Cy-Ph(F)- | F | F |
| C$_2$H$_5$ | Cy-Ph(F,F)- | F | H |
| C$_2$H$_5$ | Cy-Ph(F,F)- | F | F |
| n-C$_3$H$_7$ | Cy-Ph(F,F)- | F | H |
| n-C$_3$H$_7$ | Cy-Ph(F,F)- | F | F |

-continued
| R | —(A¹—Z¹)ₘ—A²—Z²— | L¹ | L² | |
|---|---|---|---|---|
| n-C₅H₁₁ | 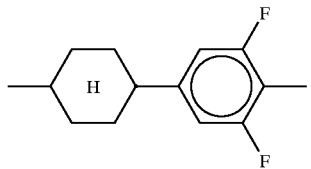 | F | H | |
| n-C₅H₁₁ | 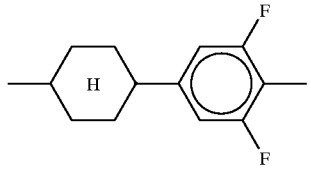 | F | F | |
| n-C₃H₇ | 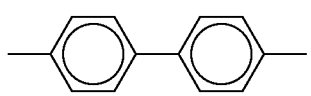 | F | H | |
| n-C₃H₇O | 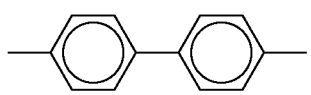 | F | H | |
| n-C₃H₇ | 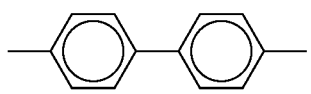 | F | F | |
| n-C₃H₇O | 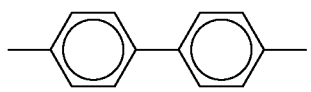 | F | F | |
| n-C₅H₁₁ | 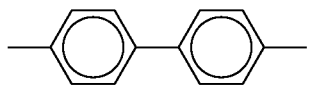 | F | H | |
| n-C₅H₁₁O | 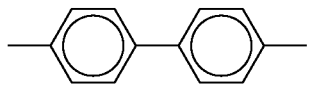 | F | H | |
| n-C₃H₇ | 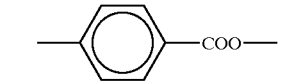 | H | H | C 84 N 139 I; Δn = +0.266; Δε = 44.88 |
| n-C₃H₇ | 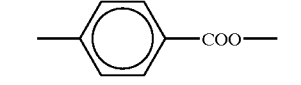 | H | F | |
| n-C₅H₁₁ | 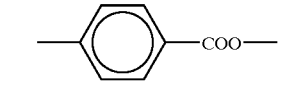 | H | H | |
| n-C₅H₁₁ | 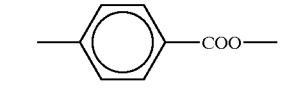 | H | F | |
| n-C₅H₁₁ | 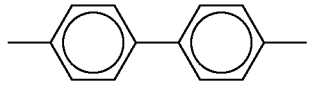 | F | F | |

-continued
| R | —(A¹—Z¹)ₘ—A²—Z²— | L¹ | L² | |
|---|---|---|---|---|
| n-C₅H₁₁O | 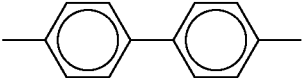 | F | F | |
| C₂H₅ | 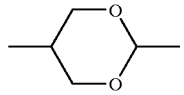 | F | H | |
| C₂H₅ | 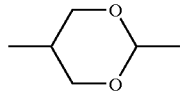 | F | F | |
| n-C₃H₇ | 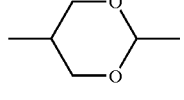 | F | H | |
| n-C₃H₇ | 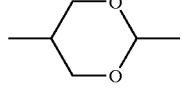 | F | F | C 71 I; Δn = +0.175; Δε = 59.78 |
| n-C₅H₁₁ | 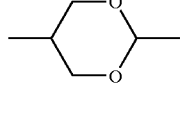 | F | H | |
| n-C₅H₁₁ | 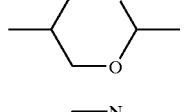 | F | F | |
| n-C₃H₇ | 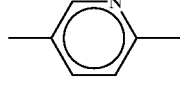 | F | F | |
| n-C₃H₇ | 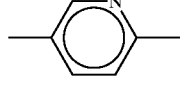 | F | H | |
| n-C₃H₇O | 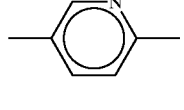 | F | H | |
| n-C₃H₇ | 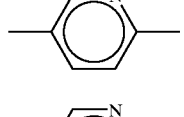 | F | F | C 136 I |
| n-C₃H₇O | 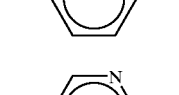 | F | F | |
| n-C₅H₁₁ |  | F | H | C 79 N 88.9 I; Δn = +0.315; Δε = 57.02 |
| n-C₃H₇ |  | H | H | C 143 N (141.6) I; |

| R | $-(A^1-Z^1)_m-A^2-Z^2-$ | $L^1$ | $L^2$ | |
|---|---|---|---|---|
| n-C$_5$H$_{11}$O | (pyridine) | F | H | |
| n-C$_5$H$_{11}$ | (pyridine) | F | F | |
| n-C$_5$H$_{11}$O | (pyridine) | F | F | |
| C$_2$H$_5$ | (fluorocyclohexene) | F | H | |
| C$_2$H$_5$ | (fluorocyclohexene) | F | F | |
| n-C$_3$H$_7$ | (difluorophenyl-COO) | H | H | C 69 N 92.4 I; Δn = +0.249; Δε = 46.7 |
| n-C$_5$H$_{11}$ | (difluorophenyl-COO) | H | F | |

EXAMPLE 2

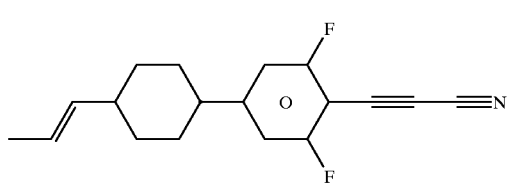

Step 2.1

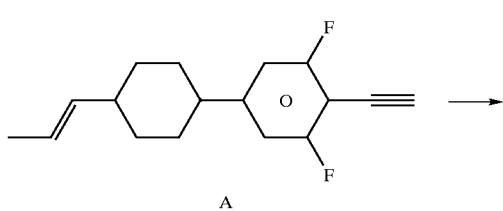

A

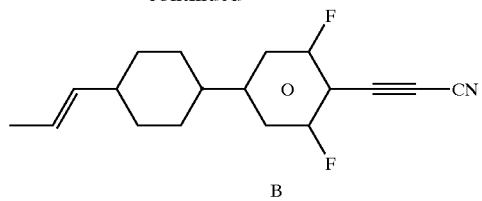

B

Under a nitrogen atmosphere, 0.019 mol of A are added with stirring to 30 ml of abs. THF. 0.021 mol of BuLi (15% solution in n-hexane) is added dropwise to the mixture at −65° C., and the mixture is then stirred for 0.5 h. After 0.021 mol of p-toluenesulfonyl cyanide in 10 ml of THF has been added at −60° C., the mixture is allowed to warm to 5° C. After hydrolysis, the solution is subjected to customary work-up. The crude product is recrystallized from ethanol and n-heptane.

The following compounds of the formula

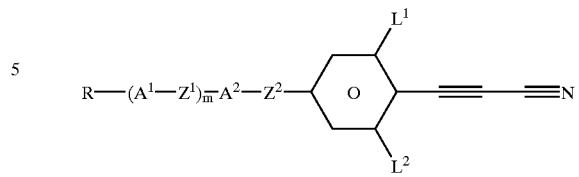

are prepared analogously:

| R | $-(A^1-Z^1)_m-A^2-Z^2-$ | $L^1$ | $L^2$ | |
|---|---|---|---|---|
| $CH_2=CH$ | 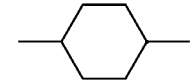 | H | H | c 65 N 120.4 I; $\Delta n = +0.279$; $\Delta\epsilon = 28.77$ |
| $CH_2=CH$ | 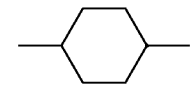 | H | F | |
| $CH_2=CH$ | 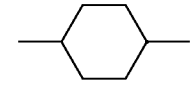 | F | F | c 69 N (49.5) I; $\Delta n = +0.220$; $\Delta\epsilon = 39.1$ |
| $CH_3CH=CH$ | 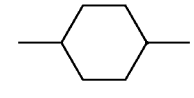 | H | H | c 99 N 172.5 I; $\Delta n = +0.295$; $\Delta\epsilon = 35.1$ |
| $CH_3CH=CH$ | 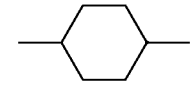 | H | F | |
| $C_2H_5CH=CH$ | 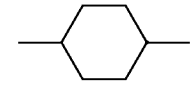 | H | H | |
| $C_2H_5CH=CH$ | 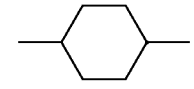 | H | F | |
| $C_2H_5CH=CH$ | 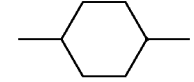 | F | F | |
| $C_3H_7CH=CH$ | 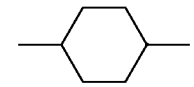 | H | H | |
| $C_3H_7CH=CH$ | 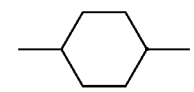 | H | F | |
| $C_3H_7CH=CH$ | 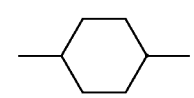 | F | F | |
| $CH_2=CHCH_2CH_2$ | 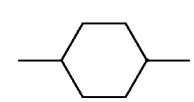 | H | H | K 65 N 133.5 I; $\Delta n = +0.265$; $\Delta\epsilon = 27.92$ |

-continued
| R | -(A¹-Z¹)ₘ-A²-Z²- | L¹ | L² | |
|---|---|---|---|---|
| CH₂=CHCH₂CH₂ |  | H | F | |
| CH₂=CHCH₂CH₂ |  | F | F | K 57 N 78.9 I; Δn = +0.209; Δε = 35.3 |
| CH₃CH=CHCH₂CH₂ |  | H | H | |
| CH₃CH=CHCH₂CH₂ |  | H | F | |
| CH₃CH=CHCH₂CH₂ | 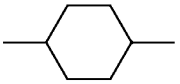 | F | F | |
| C₂H₅CH=CHCH₂CH₂ |  | H | H | |
| C₂H₅CH=CHCH₂CH₂ | 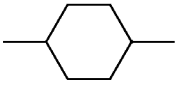 | H | F | |
| C₂H₅CH=CHCH₂CH₂ | 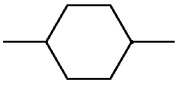 | F | F | |
| C₃H₇CH=CHCH₂CH₂ |  | H | H | |
| C₃H₇CH=CHCH₂CH₂ |  | H | F | |
| C₃H₇CH=CHCH₂CH₂ | 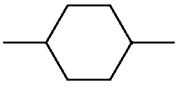 | F | F | |
| CH₂=CH— | 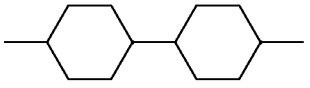 | H | F | |
| CH₃CH=CH— | 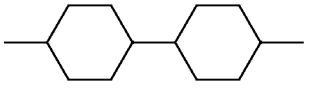 | H | F | |
| C₂H₅CH=CH— | 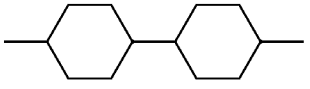 | H | F | |
| C₃H₇—CH=CH— | 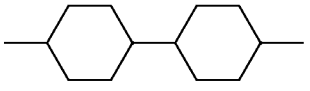 | H | F | |

-continued
| R | -(A¹-Z¹)ₘ-A²-Z²- | L¹ | L² |
|---|---|---|---|
| CH₂=CH |  | H | H |
| CH₂=CH—O— |  | H | H |
| CH₂=CH |  | H | F |
| CH₂=CH—O— |  | H | F |
| CH₂=CH |  | F | F |
| CH₂=CH—O— |  | F | F |
| CH₃CH=CH |  | H | H |
| CH₃CH=CH |  | H | F |
| CH₃CH=CH |  | F | F |
| C₂H₅CH=CH |  | H | H |
| C₂H₅CH=CH | 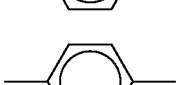 | H | F |
| C₂H₅CH=CH | 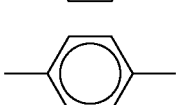 | F | F |
| C₃H₇CH=CH | 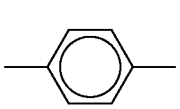 | H | H |
| C₃H₇CH=CH | 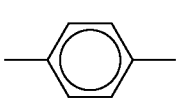 | H | F |
| C₃H₇CH=CH |  | F | F |

-continued
| R | -(A¹-Z¹)ₘ-A²-Z²- | L¹ | L² |
|---|---|---|---|
| CH₂=CHCH₂CH₂ |  | H | H |
| CH₂=CHCH₂CH₂ |  | H | F |
| CH₂=CHCH₂CH₂ |  | F | F |
| CH₃CH=CHCH₂CH₂ | 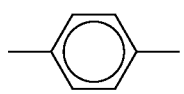 | H | H |
| CH₃CH=CHCH₂CH₂ | 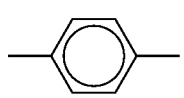 | H | F |
| CH₃CH=CHCH₂CH₂ | 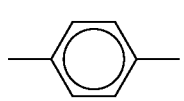 | F | F |
| C₂H₅CH=CHCH₂CH₂ | 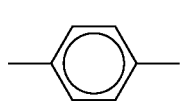 | H | H |
| C₂H₅CH=CHCH₂CH₂ | 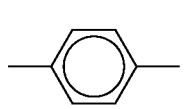 | H | F |
| C₂H₅CH=CHCH₂CH₂ | 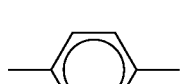 | F | F |
| C₃H₇CH=CHCH₂CH₂ | 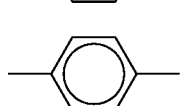 | H | H |
| C₃H₇CH=CHCH₂CH₂ | 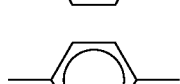 | H | F |
| C₃H₇CH=CHCH₂CH₂ |  | F | F |
| CH₂=CH | 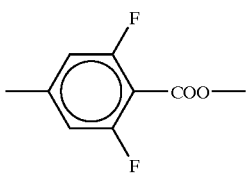 | H | H |
| CH₂=CH | 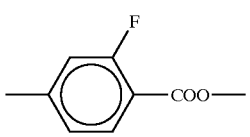 | H | H |

-continued

| R | -(A¹-Z¹)ₘ-A²-Z²- | L¹ | L² |
|---|---|---|---|
| CH₃—CH=CH | 2,6-difluoro-4-methylphenyl-COO— | H | H |
| CH₃—CH=CH | 2-fluoro-4-methylphenyl-COO— | H | H |
| CH₂=CH | 1,3-dioxane-2,5-diyl | H | H |
| CH₂=CH | 1,3-dioxane-2,5-diyl | H | F |
| CH₂=CH | 1,3-dioxane-2,5-diyl | F | F |
| CH₃CH=CH | 1,3-dioxane-2,5-diyl | H | H |
| CH₃CH=CH | 1,3-dioxane-2,5-diyl | H | F |
| CH₃CH=CH | 1,3-dioxane-2,5-diyl | F | F |
| C₂H₅CH=CH | 1,3-dioxane-2,5-diyl | H | H |
| C₂H₅CH=CH | 1,3-dioxane-2,5-diyl | H | F |
| C₂H₅CH=CH | 1,3-dioxane-2,5-diyl | F | F |
| C₃H₇CH=CH | 1,3-dioxane-2,5-diyl | H | H |
| C₃H₇CH=CH | 1,3-dioxane-2,5-diyl | H | F |

-continued

| R | -(A$^1$-Z$^1$)$_m$-A$^2$-Z$^2$- | L$^1$ | L$^2$ |
|---|---|---|---|
| C$_3$H$_7$CH=CH | 1,3-dioxane | F | F |
| CH$_2$=CHCH$_2$CH$_2$ | 1,3-dioxane | H | H |
| CH$_2$=CHCH$_2$CH$_2$ | 1,3-dioxane | H | F |
| CH$_2$=CHCH$_2$CH$_2$ | 1,3-dioxane | F | F |
| CH$_3$CH=CHCH$_2$CH$_2$ | 1,3-dioxane | H | H |
| CH$_3$CH=CHCH$_2$CH$_2$ | 1,3-dioxane | H | F |
| CH$_3$CH=CHCH$_2$CH$_2$ | 1,3-dioxane | F | F |
| C$_2$H$_5$CH=CHCH$_2$CH$_2$ | 1,3-dioxane | H | H |
| C$_2$H$_5$CH=CHCH$_2$CH$_2$ | 1,3-dioxane | H | F |
| C$_2$H$_5$CH=CHCH$_2$CH$_2$ | 1,3-dioxane | F | F |
| C$_3$H$_7$CH=CHCH$_2$CH$_2$ | 1,3-dioxane | H | H |
| C$_3$H$_7$CH=CHCH$_2$CH$_2$ | 1,3-dioxane | H | F |
| C$_3$H$_7$CH=CHCH$_2$CH$_2$ | 1,3-dioxane | F | F |
| CH$_2$=CH | pyridine | H | H |

-continued
| R | -(A¹-Z¹)ₘ-A²-Z²- | L¹ | L² |
|---|---|---|---|
| CH₂=CH | 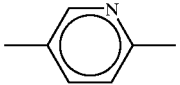 | H | F |
| CH₂=CH |  | F | F |
| CH₃CH=CH | 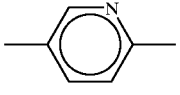 | H | H |
| CH₃CH=CH |  | H | F |
| CH₃CH=CH | 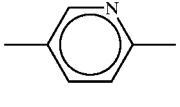 | F | F |
| C₂H₅CH=CH | 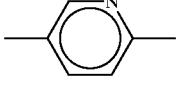 | H | H |
| C₂H₅CH=CH | 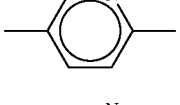 | H | F |
| C₂H₅CH=CH | 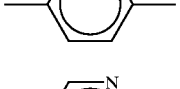 | F | F |
| C₃H₇CH=CH | 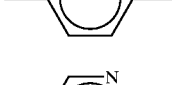 | H | H |
| C₃H₇CH=CH | 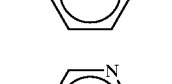 | H | F |
| C₃H₇CH=CH | 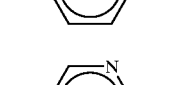 | F | F |
| CH₂=CHCH₂CH₂ | 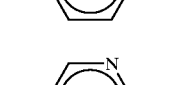 | H | H |
| CH₂=CHCH₂CH₂ | 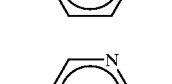 | H | F |
| CH₂=CHCH₂CH₂ |  | F | F |

-continued

| R | -(A¹-Z¹)ₘ-A²-Z²- | L¹ | L² |
|---|---|---|---|
| CH₃CH=CHCH₂CH₂ | pyridine (3,6) | H | H |
| CH₃CH=CHCH₂CH₂ | pyridine (3,6) | H | F |
| CH₃CH=CHCH₂CH₂ | pyridine (3,6) | F | F |
| C₂H₅CH=CHCH₂CH₂ | pyridine (3,6) | H | H |
| C₂H₅CH=CHCH₂CH₂ | pyridine (3,6) | H | F |
| C₂H₅CH=CHCH₂CH₂ | pyridine (3,6) | F | F |
| C₃H₇CH=CHCH₂CH₂ | pyridine (3,6) | H | H |
| C₃H₇CH=CHCH₂CH₂ | pyridine (3,6) | H | F |
| C₃H₇CH=CHCH₂CH₂ | pyridine (3,6) | F | F |
| CH₂=CH | pyrimidine (2,5) | H | H |
| CH₂=CH | pyrimidine (2,5) | H | F |
| CH₂=CH | pyrimidine (2,5) | F | F |
| CH₃CH=CH | pyrimidine (2,5) | H | H |
| CH₃CH=CH | pyrimidine (2,5) | H | F |

-continued
| R | -(A¹-Z¹)ₘ-A²-Z²- | L¹ | L² |
|---|---|---|---|
| CH₃CH=CH |  | F | F |
| C₂H₅CH=CH | 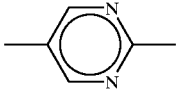 | H | H |
| C₂H₅CH=CH | 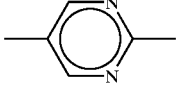 | H | F |
| C₂H₅CH=CH | 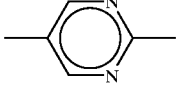 | F | F |
| C₃H₇CH=CH | 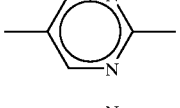 | H | H |
| C₃H₇CH=CH | 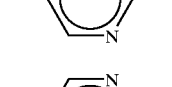 | H | F |
| C₃H₇CH=CH | 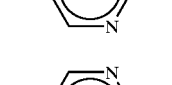 | F | F |
| CH₂=CHCH₂CH₂ | 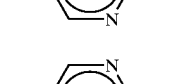 | H | H |
| CH₂=CHCH₂CH₂ | 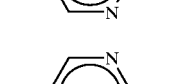 | H | F |
| CH₂=CHCH₂CH₂ | 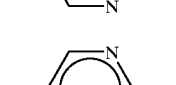 | F | F |
| CH₃CH=CHCH₂CH₂ | 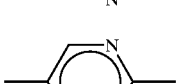 | H | H |
| CH₃CH=CHCH₂ | 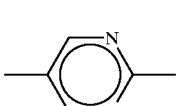 | H | F |
| CH₃CH=CHCH₂ | 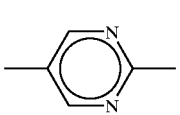 | F | F |
| C₂H₅CH=CHCH₂ |  | H | H |

-continued
| R | -(A¹-Z¹)$_m$-A²-Z²- | L¹ | L² |
|---|---|---|---|
| C$_2$H$_5$CH=CHCH$_2$CH$_2$ | 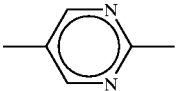 | H | F |
| C$_2$H$_5$CH=CHCH$_2$CH$_2$ |  | F | F |
| C$_3$H$_7$CH=CHCH$_2$CH$_2$ |  | H | H |
| C$_3$H$_7$CH=CHCH$_2$CH$_2$ | 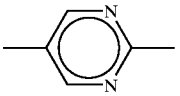 | H | F |
| C$_3$H$_7$CH=CHCH$_2$CH$_2$ | 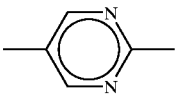 | F | F |
| CH$_2$=CH | 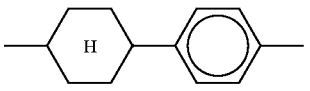 | H | H |
| CH$_2$=CH | 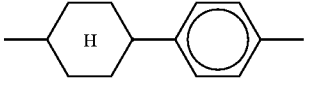 | H | F |
| CH$_2$=CH | 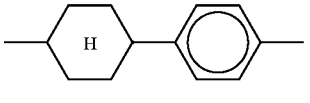 | F | F |
| CH$_3$CH=CH | 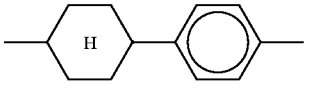 | H | H |
| CH$_3$CH=CH | 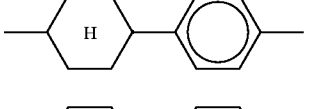 | H | F |
| CH$_3$CH=CH | 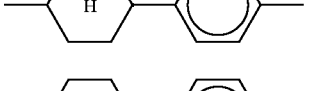 | F | F |
| C$_2$H$_5$CH=CH |  | H | H |
| C$_2$H$_5$CH=CH | 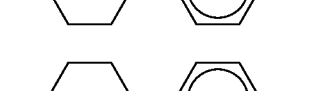 | H | F |
| C$_2$H$_5$CH=CH |  | F | F |

-continued
| R | -(A¹-Z¹)$_m$-A²-Z²- | L¹ | L² |
|---|---|---|---|
| C$_3$H$_7$CH=CH | 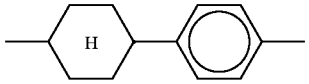 | H | H |
| C$_3$H$_7$CH=CH | 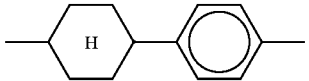 | H | F |
| C$_3$H$_7$CH=CH | 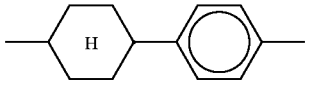 | F | F |
| CH$_2$=CHCH$_2$CH$_2$ | 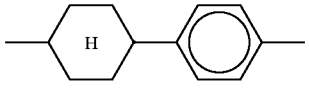 | H | H |
| CH$_2$=CHCH$_2$CH$_2$ | 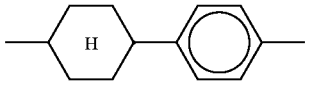 | H | F |
| CH$_2$=CHCH$_2$CH$_2$ | 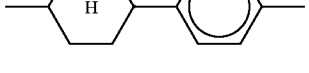 | F | F |
| CH$_3$CH=CHCH$_2$CH$_2$ |  | H | H |
| CH$_3$CH=CHCH$_2$CH$_2$ |  | H | F |
| CH$_3$CH=CHCH$_2$CH$_2$ |  | F | F |
| C$_2$H$_5$CH=CH$_2$CH$_2$ |  | H | H |
| C$_2$H$_5$CH=CH$_2$CH$_2$ |  | H | F |
| C$_2$H$_5$CH=CH$_2$CH$_2$ |  | F | F |
| C$_3$H$_7$CH=CHCH$_2$CH$_2$ | 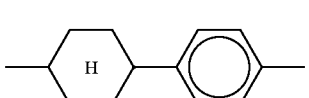 | H | H |
| C$_3$H$_7$CH=CHCH$_2$CH$_2$ | 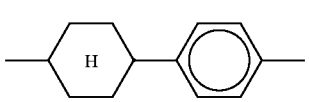 | H | F |
| C$_3$H$_7$CH=CHCH$_2$CH$_2$ |  | F | F |

-continued

| R | -(A¹-Z¹)ₘ-A²-Z²- | L¹ | L² |
|---|---|---|---|
| CH₂=CH | —[H]—[⌬(F)]— | H | H |
| CH₂=CH | —[H]—[⌬(F)]— | H | F |
| CH₂=CH | —[H]—[⌬(F)]— | F | F |
| CH₃CH=CH | —[H]—[⌬(F)]— | H | H |
| CH₃CH=CH | —[H]—[⌬(F)]— | H | F |
| CH₃CH=CH | —[H]—[⌬(F)]— | F | F |
| C₂H₅CH=CH | —[H]—[⌬(F)]— | H | H |
| C₂H₅CH=CH | —[H]—[⌬(F)]— | H | F |
| C₂H₅CH=CH | —[H]—[⌬(F)]— | F | F |
| C₃H₇CH=CH | —[H]—[⌬(F)]— | H | H |
| C₃H₇CH=CH | —[H]—[⌬(F)]— | H | F |

-continued
| R | -(A¹-Z¹)ₘ-A²-Z²- | L¹ | L² |
|---|---|---|---|
| $C_3H_7CH=CH$ | 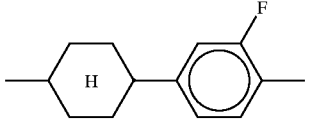 | F | F |
| $CH_2=CHCH_2CH_2$ | 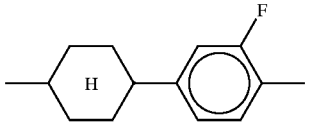 | H | H |
| $CH_2=CHCH_2CH_2$ | 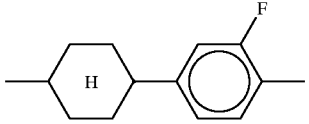 | H | F |
| $CH_2=CHCH_2CH_2$ | 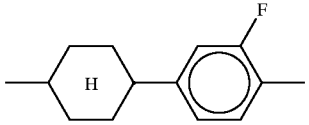 | F | F |
| $CH_3CH=CHCH_2CH_2$ | 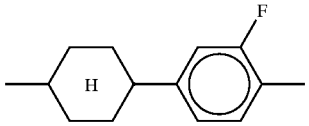 | H | H |
| $CH_3CH=CHCH_2CH_2$ | 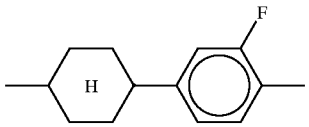 | H | F |
| $CH_3CH=CHCH_2CH_2$ | 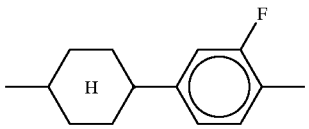 | F | F |
| $C_2H_5CH=CHCH_2CH_2$ | 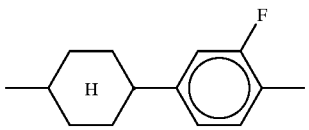 | H | H |
| $C_2H_5CH=CHCH_2CH_2$ | 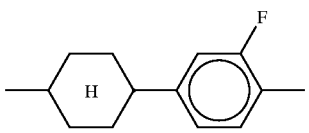 | H | F |
| $C_2H_5CH=CHCH_2CH_2$ | 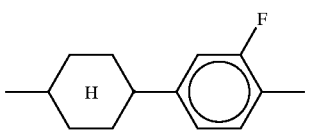 | F | F |
| $C_3H_7CH=CHCH_2CH_2$ | 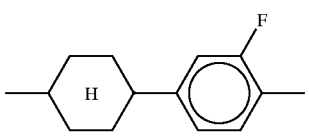 | H | H |

-continued

| R | -(A¹-Z¹)ₘ-A²-Z²- | L¹ | L² |
|---|---|---|---|
| $C_3H_7CH=CHCH_2CH_2$ | [cyclohexyl-phenyl, ring F at upper position] | H | F |
| $C_3H_7CH=CHCH_2CH_2$ | [cyclohexyl-phenyl, ring F at upper position] | F | F |
| $CH_2=CH$ | [cyclohexyl-phenyl, ring F upper and lower] | H | H |
| $CH_2=CH$ | [cyclohexyl-phenyl, ring F upper and lower] | H | F |
| $CH_2=CH$ | [cyclohexyl-phenyl, ring F upper and lower] | F | F |
| $CH_3CH=CH$ | [cyclohexyl-phenyl, ring F upper and lower] | H | H |
| $CH_3CH=CH$ | [cyclohexyl-phenyl, ring F upper and lower] | H | F |
| $CH_3CH=CH$ | [cyclohexyl-phenyl, ring F upper and lower] | F | F |
| $C_2H_5CH=CH$ | [cyclohexyl-phenyl, ring F upper and lower] | H | H |

-continued

| R | -(A¹-Z¹)ₘ-A²-Z²- | L¹ | L² |
|---|---|---|---|
| C₂H₅CH=CH | Cy-Ph(F,F) [3,5-diF] | H | F |
| C₂H₅CH=CH | Cy-Ph(F,F) [3,5-diF] | F | F |
| C₃H₇CH=CH | Cy-Ph(F,F) [3,5-diF] | H | H |
| C₃H₇CH=CH | Cy-Ph(F,F) [3,5-diF] | H | F |
| C₃H₇CH=CH | Cy-Ph(F,F) [3,5-diF] | F | F |
| CH₂=CHCH₂ | Cy-Ph(F,F) [3,5-diF] | H | H |
| C₃H₇CH=CHCH₂ | Cy-Ph(F,F) [3,5-diF] | H | F |
| C₃H₇CH=CHCH₂ | Cy-Ph(F,F) [3,5-diF] | F | F |
| CH₂=CH | Ph-Ph | H | H |

-continued
| R | -(A¹-Z¹)ₘ-A²-Z²- | L¹ | L² |
|---|---|---|---|
| CH₂=CH | 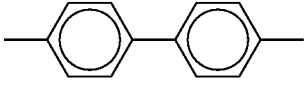 | H | F |
| CH₂=CH | 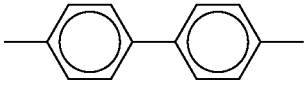 | F | F |
| CH₃CH=CH | 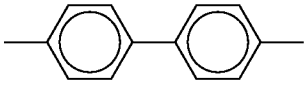 | H | H |
| CH₃CH=CH | 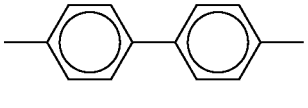 | H | F |
| CH₃CH=CH | 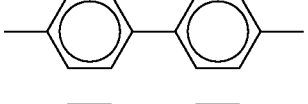 | F | F |
| C₂H₅CH=CH |  | H | H |
| C₂H₅CH=CH |  | H | F |
| C₂H₅CH=CH |  | F | F |
| C₃H₇CH=CH |  | H | H |
| C₃H₇CH=CH |  | H | F |
| C₃H₇CH=CH |  | F | F |
| CH₂=CHCH₂CH₂ |  | H | H |
| CH₂=CHCH₂CH₂ | 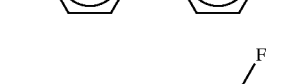 | H | F |
| CH₂=CHCH₂CH₂ | 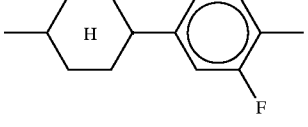 | H | F |

-continued

| R | -(A¹-Z¹)ₘ-A²-Z²- | L¹ | L² |
|---|---|---|---|
| CH₂=CHCH₂CH₂ | cyclohexyl-phenyl(2,6-diF) | F | F |
| CH₃CH=CHCH₂CH₂ | cyclohexyl-phenyl(2,6-diF) | H | H |
| CH₃CH=CHCH₂CH₂ | cyclohexyl-phenyl(2,6-diF) | H | F |
| CH₃CH=CHCH₂CH₂ | cyclohexyl-phenyl(2,6-diF) | F | F |
| C₂H₅CH=CHCH₂CH₂ | cyclohexyl-phenyl(2,6-diF) | H | H |
| C₂H₅CH=CHCH₂CH₂ | cyclohexyl-phenyl(2,6-diF) | H | F |
| C₂H₅CH=CHCH₂CH₂ | cyclohexyl-phenyl(2,6-diF) | F | F |
| C₃H₇CH=CHCH₂CH₂ | cyclohexyl-phenyl(2,6-diF) | H | H |
| CH₂=CHCH₂CH₂ | phenyl-phenyl | F | F |

-continued
| R | -(A¹-Z¹)ₘ-A²-Z²- | L¹ | L² |
|---|---|---|---|
| CH₃CH=CHCH₂CH₂ | 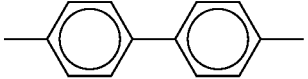 | H | H |
| CH₃CH=CHCH₂CH₂ | 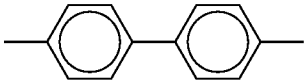 | H | F |
| CH₃CH=CHCH₂CH₂ | 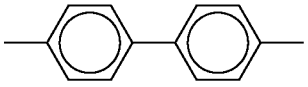 | F | F |
| C₂H₅CH=CHCH₂ | 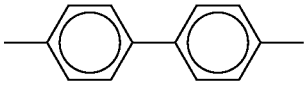 | H | H |
| C₂H₅CH=CHCH₂ | 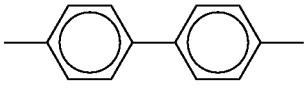 | H | F |
| C₂H₅CH=CHCH₂ | 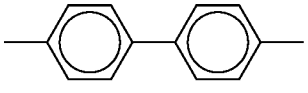 | F | F |
| C₃H₇CH=CHCH₂ | 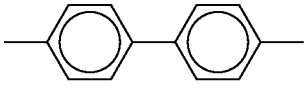 | H | H |
| C₃H₇CH=CHCH₂ | 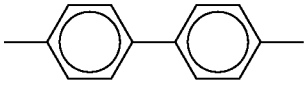 | H | F |
| C₃H₇CH=CHCH₂ | 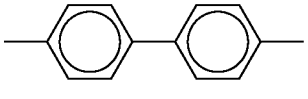 | F | F |
| CH₂=CH | 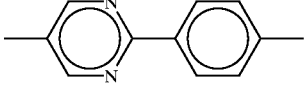 | H | H |
| CH₂=CH | 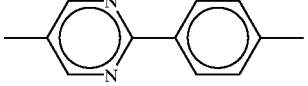 | H | F |
| CH₂=CH | 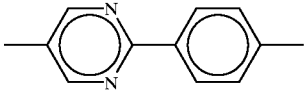 | F | F |
| CH₃CH=CH | 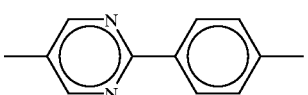 | H | H |
| CH₃CH=CH | 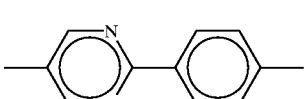 | H | F |

-continued
| R | -(A¹-Z¹)ₘ-A²-Z²- | L¹ | L² |
|---|---|---|---|
| CH₃CH=CH | 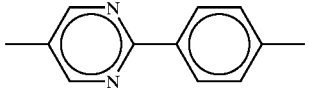 | F | F |
| CH₂=CHCH₂CH₂ | 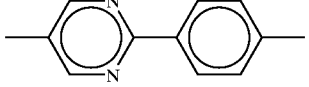 | H | H |
| CH₂=CHCH₂CH₂ | 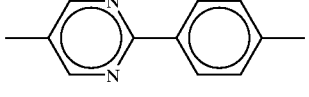 | H | F |
| CH₂=CHCH₂CH₂ | 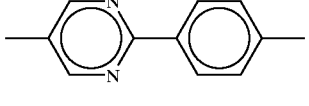 | F | F |
| CH₃CH=CHCH₂CH₂ | 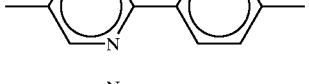 | H | H |
| CH₃CH=CHCH₂CH₂ |  | H | F |
| CH₃CH=CHCH₂CH₂ |  | F | F |
| CH₂=CH |  | H | H |
| CH₂=CH |  | H | F |
| CH₂=CH |  | F | F |
| CH₃CH=CH | 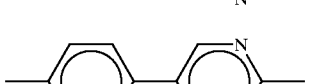 | H | H |
| CH₃CH=CH | 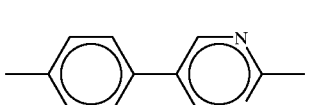 | H | F |
| CH₃CH=CH | 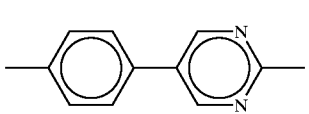 | F | F |
| CH₂=CHCH₂CH₂ |  | H | H |

-continued
| R | -(A$^1$-Z$^1$)$_m$-A$^2$-Z$^2$- | L$^1$ | L$^2$ |
|---|---|---|---|
| CH$_2$=CHCH$_2$CH$_2$ | 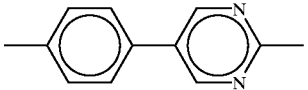 | H | F |
| CH$_2$=CHCH$_2$CH$_2$ | 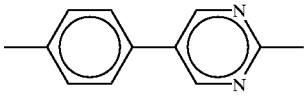 | F | F |
| CH$_3$CH=CHCH$_2$ | 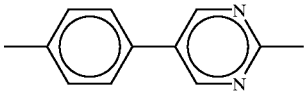 | H | H |
| CH$_3$CH=CHCH$_2$ | 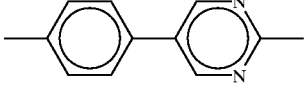 | H | F |
| CH$_3$CH=CHCH$_2$ | 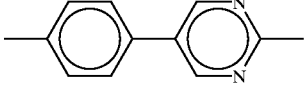 | F | F |
| CH$_2$=CH | 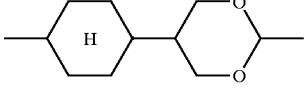 | H | H |
| CH$_2$=CH | 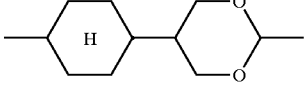 | H | F |
| CH$_2$=CH | 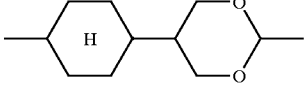 | F | F |
| CH$_3$CH=CH | 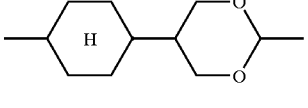 | H | H |
| CH$_3$CH=CH | 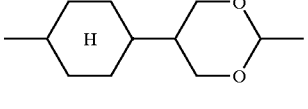 | H | F |
| CH$_3$CH=CH | 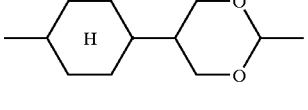 | F | F |
| CH$_2$=CHCH$_2$ | 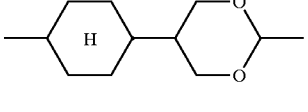 | H | H |
| CH$_2$=CHCH$_2$ | 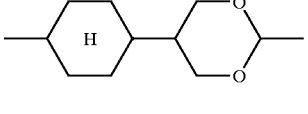 | H | F |

-continued

| R | -(A¹-Z¹)ₘ-A²-Z²- | L¹ | L² |
|---|---|---|---|
| CH₂=CHCH₂CH₂ | cyclohexyl-1,3-dioxane | F | F |
| CH₃CH=CHCH₂CH₂ | cyclohexyl-1,3-dioxane | H | H |
| CH₃CH=CHCH₂CH₂ | cyclohexyl-1,3-dioxane | H | F |
| CH₃CH=CHCH₂CH₂ | cyclohexyl-1,3-dioxane | F | F |
| CH₂=CH | fluorocyclohexenyl | H | H |
| CH₂=CH | fluorocyclohexenyl | H | F |
| CH₂=CH | fluorocyclohexenyl | F | F |
| CH₃CH=CH | fluorocyclohexenyl | H | H |
| CH₃CH=CH | fluorocyclohexenyl | H | F |
| CH₃CH=CH | fluorocyclohexenyl | F | F |
| CH₂=CHCH₂CH₂ | fluorocyclohexenyl | H | H |

-continued

| R | $-(A^1-Z^1)_m-A^2-Z^2-$ | $L^1$ | $L^2$ |
|---|---|---|---|
| $CH_2=CHCH_2CH_2$ | cyclohexene with F | H | F |
| $CH_2=CHCH_2CH_2$ | cyclohexene with F | F | F |
| $CH_3CH=CHCH_2CH_2$ | cyclohexene with F | H | H |
| $CH_3CH=CHCH_2CH_2$ | cyclohexene with F | H | F |
| $CH_3CH=CHCH_2CH_2$ | cyclohexene with F | F | F |

Mixture Examples

Example A

| | | | |
|---|---|---|---|
| PCH-5F | 9.0% | Clearing point [° C.]: 87.8 | |
| PCH-6F | 7.2% | $\Delta n$ [589 nm, 20° C.]: 0.1074 | |
| PCH-7F | 5.4% | $\Delta \epsilon$ [1 kHz, 20° C.]: 8.95 | |
| CCP-2OCF$_3$ | 7.2% | $\nu_{20}$ [mm$^2 \cdot$ s$^{-1}$]: 15.0 | |
| CCP-3OCF$_3$ | 10.8% | | |
| CCP-4OCF$_3$ | 6.3% | | |
| CCP-5OCF$_3$ | 9.9% | | |
| BCH-3F.F | 10.8% | | |
| BCH-5F.F | 9.0% | | |
| ECCP-3OCF$_3$ | 4.5% | | |
| ECCP-5OCF$_3$ | 4.5% | | |
| CBC-33F | 1.8% | | |
| CBC-53F | 1.8% | | |
| CBC-55F | 1.8% | | |
| CU-3-AN | 10.0% | | |

Example B

| | | | |
|---|---|---|---|
| PCH-5F | 9.0% | Clearing point [° C.]: 90.8 | |
| PCH-6F | 7.2% | $\Delta n$ [589 nm, 20° C.]: 0.1101 | |
| PCH-7F | 5.4% | $\Delta \epsilon$ [1 kHz, 20° C.]: 8.32 | |
| CCP-2OCF$_3$ | 7.2% | $\nu_{20}$ [mm$^2 \cdot$ s$^{-1}$]: 14.0 | |
| CCP-3OCF$_3$ | 10.8% | | |
| CCP-4OCF$_3$ | 6.3% | | |
| CCP-5OCF$_3$ | 9.9% | | |
| BCH-3F.F | 10.8% | | |
| BCH-5F.F | 9.0% | | |
| ECCP-3OCF$_3$ | 4.5% | | |

-continued

| | |
|---|---|
| ECCP-5OCF$_3$ | 4.5% |
| CBC-33F | 1.8% |
| CBC-53F | 1.8% |
| CBC-55F | 1.8% |
| CG-3-AN | 10.0% |

Example C

| | | | |
|---|---|---|---|
| PCH-5F | 9.0% | Clearing point [° C.]: 89.1 | |
| PCH-6F | 7.2% | $\Delta n$ [589 nm, 20° C.]: +0.1070 | |
| PCH-7F | 5.4% | $\Delta \epsilon$ [1 kHz, 20° C.]: 8.61 | |
| CCP-2OCF$_3$ | 7.2% | $\nu_{20}$ [mm$^2 \cdot$ s$^{-1}$]: 15 | |
| CCP-3OCF$_3$ | 10.8% | | |
| CCP-4OCF$_3$ | 6.3% | | |
| CCP-5OCF$_3$ | 9.9% | | |
| BCH-3F.F | 10.8% | | |
| BCH-5F.F | 9.0% | | |
| ECCP-3OCF$_3$ | 4.5% | | |
| ECCP-5OCF$_3$ | 4.5% | | |
| CBC-33F | 1.8% | | |
| CBC-53F | 1.8% | | |
| CBC-55F | 1.8% | | |
| CU-5-AN | 10.0% | | |

Example D

| | | | |
|---|---|---|---|
| PCH-5F | 9.0% | Clearing point [° C.]: 83.2 | |

-continued

| | | |
|---|---|---|
| PCH-6F | 7.2% | Δn [589 nm, 20° C.]: 0.1055 |
| PCH-7F | 5.4% | Δε [1 kHz, 20° C.]: 8.80 |
| CCP-2OCF$_3$ | 7.2% | ν$_{20}$ [mm$^2$ · s$^{-1}$]: 15 |
| CCP-3OCF$_3$ | 10.8% | |
| CCP-4OCF$_3$ | 6.3% | |
| CCP-5OCF$_3$ | 9.9% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| CU-2-AN | 10.0% | |

Example E

| | | |
|---|---|---|
| PCH-5F | 9.0% | Clearing point [° C.]: 86.8 |
| PCH-6F | 7.2% | Δn [589 nm, 20° C.]: 0.1206 |
| PCH-7F | 5.4% | Δε [1 kHz, 20° C.]: 9.88 |
| CCP-2OCF$_3$ | 7.2% | ν$_{20}$ [mm$^2$ · s$^{-1}$]: 14 |
| CCP-3OCF$_3$ | 10.8% | |
| CCP-4OCF$_3$ | 6.3% | |
| CCP-5OCF$_3$ | 9.9% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| PU-3-AN | 10.0% | |

Example F

| | | |
|---|---|---|
| PCH-5F | 9.0% | Clearing point [° C.]: 85.2 |
| PCH-6F | 7.2% | Δn [589 nm, 20° C.]: 0.1051 |
| PCH-7F | 5.4% | Δε [1 kHz, 20° C.]: 10.71 |
| CCP-2OCF$_3$ | 7.2% | ν$_{20}$ [mm$^2$ · s$^{-1}$]: 15 |
| CCP-3OCF$_3$ | 10.8% | |
| CCP-4OCF$_3$ | 6.3% | |
| CCP-5OCF$_3$ | 9.9% | |
| BCH-3F.F | 10.8% | |
| BCH-5F.F | 9.0% | |
| ECCP-3OCF$_3$ | 4.5% | |
| ECCP-5OCF$_3$ | 4.5% | |
| CBC-33F | 1.8% | |
| CBC-53F | 1.8% | |
| CBC-55F | 1.8% | |
| DU-3-AN | 10.0% | |

Example G

| | | |
|---|---|---|
| PCH-6F | 7.20% | Clearing point [° C.]: +93.8 |
| PCH-7F | 5.40% | Δn [589.3 nm, 20° C.]: +0.1146 |
| CCP-2OCF$_3$ | 7.20% | Δε [1 kHz, 20° C.]: +7.6 |
| CCP-3OCF$_3$ | 10.80% | ν$_{20}$ [mm$^2$ · s$^{-1}$]: 14 |
| CCP-4OCF$_3$ | 6.30% | |
| PCH-5F | 9.00% | |
| CCP-5OCF$_3$ | 9.90% | |
| BCH-3F.F | 10.80% | |
| BCH-5F.F | 9.00% | |
| ECCP-3OCF$_3$ | 4.50% | |
| ECCP-5OCF$_3$ | 4.50% | |
| CBC-33F | 1.80% | |

-continued

| | | |
|---|---|---|
| CBC-53F | 1.80% | |
| CBC-55F | 1.80% | |
| CP-V-AN | 10.00% | |

Example H

| | | |
|---|---|---|
| BCH-3F.F | 10.80% | Clearing point [° C.]: 98.5 |
| BCH-5F.F | 9.00% | Δn [589.3 nm, 20° C.]: +0.1162 |
| ECCP-3OCF$_3$ | 4.50% | Δε [1 kHz, 20° C.]: +8.2 |
| ECCP-5OCF$_3$ | 4.50% | ν$_{20}$ [mm$^2$ · s$^{-1}$]: 14 |
| CBC-33F | 1.80% | |
| CBC-53F | 1.80% | |
| CBC-55F | 1.80% | |
| PCH-6F | 7.20% | |
| PCH-7F | 5.40% | |
| CCP-2OCF$_3$ | 7.20% | |
| CCP-3OCF$_3$ | 10.80% | |
| CCP-4OCF$_3$ | 6.30% | |
| CCP-5OCF$_3$ | 9.90% | |
| PCH-5F | 9.00% | |
| CP-1V-AN | 10.00% | |

Example I

| | | |
|---|---|---|
| PCH-6F | 7.20% | Clearing point [° C.]: +95.2 |
| PCH-7F | 5.40% | Δn [589.3 nm, 20° C.]: +0.1133 |
| CCP-2OCF$_3$ | 7.20% | Δε [1 kHz, 20° C.]: +7.5 |
| CCP-3OCF$_3$ | 10.80% | ν$_{20}$ [mm$^2$ · s$^{-1}$]: 15 |
| CCP-4OCF$_3$ | 6.30% | |
| PCH-5F | 9.00% | |
| CCP-5OCF$_3$ | 9.90% | |
| BCH-3F.F | 10.80% | |
| BCH-5F.F | 9.00% | |
| ECCP-3OCF$_3$ | 4.50% | |
| ECCP-5OCF$_3$ | 4.50% | |
| CBC-33F | 1.80% | |
| CBC-53F | 1.80% | |
| CBC-55F | 1.80% | |
| CP-V2-AN | 10.00% | |

Example J

| | | |
|---|---|---|
| BCH-3F.F | 10.81% | Clearing point [° C.]: 86.5 |
| BCH-5F.F | 9.01% | Δn [589.3 nm, 20° C.]: +0.1087 |
| ECCP-3OCF$_3$ | 4.50% | Δε [1 kHz, 20° C.]: +8.6 |
| ECCP-5OCF$_3$ | 4.50% | |
| CBC-33F | 1.80% | |
| CBC-53F | 1.80% | |
| CBC-55F | 1.80% | |
| PCH-6F | 7.21% | |
| PCH-7F | 5.40% | |
| CCP-2OCF$_3$ | 7.20% | |
| CCP-3OCF$_3$ | 10.81% | |
| CCP-4OCF$_3$ | 6.30% | |
| CCP-5OCF$_3$ | 9.91% | |
| PCH-5F | 9.01% | |
| CU-V-AN | 9.94% | |

Example K

| | | | |
|---|---|---|---|
| PCH-6F | 7.20% | Clearing point [° C.]: | +87.8 |
| PCH-7F | 5.40% | Δn [589.3 nm, 20° C.]: | +0.1077 |
| CCP-2OCF$_3$ | 7.20% | Δε [1 kHz, 20° C.]: | +8.3 |
| CCP-3OCF$_3$ | 10.80% | ν$_{20}$ [mm$^2$ · s$^{-1}$]: | 15 |
| CCP-4OCF$_3$ | 6.30% | | |
| PCH-5F | 9.00% | | |
| CCP-5OCF$_3$ | 9.90% | | |
| BCH-3F.F | 10.80% | | |
| BCH-5F.F | 9.00% | | |
| ECCP-3OCF$_3$ | 4.50% | | |
| ECCP-5OCF$_3$ | 4.50% | | |
| CBC-33F | 1.80% | | |
| CBC-53F | 1.80% | | |
| CBC-55F | 1.80% | | |
| CU-V2-AN | 10.00% | | |

What is claimed is:

1. An acetylene derivative of the formula I

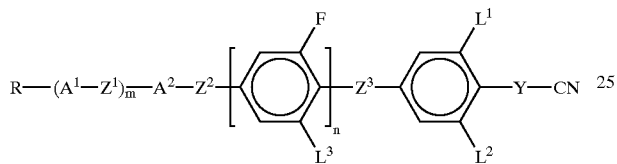

in which

R is an alkyl or alkenyl radical having 1 to 15 carbon atoms which is unsubstituted, monosubstituted by CN or CF$_3$ or at least monosubstituted by halogen, where, in addition, one or more —CH$_2$— groups in these radicals may be replaced, in each case independently of one another, by —O—, —S—,

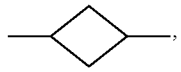

—CO—, —CO—O—, —O—O— or —O—CO—O— in such a way that O atoms are not linked directly to one another, A$^1$ and A$^2$ are each, independently of one another,
(a) a trans-1,4-cyclohexylene radical, in which, in addition, one or more nonadjacent —CH$_2$— groups may be replaced by —O— and/or —S—,
(b) a 1,4-phenylene radical, in which, in addition, one or two CH groups may be replaced by N,
(c) trans-1,4-cyclohexenylene,
(d) a radical from the group consisting of 1,4-bicyclo [2.2.2]octylene, piperidine-1,4-diyl, naphthalene-2,6-diyl, decahydronaphthalene-2,6-diyl and 1,2,3,4-tetrahydronaphthalene, 2,6-diyl,
where the radicals (a) to (c) may be monosubstituted or disubstituted by fluorine or CH$_3$, Z$^1$, Z$^2$ and Z$^3$ are each, independently of one another, —CO—O—, —O—CO—, —CH$_2$O—, —OCH$_2$—, —CH$_2$CH$_2$—, —CH=CH—, —C≡C—, —(CH$_2$)$_4$—, —OCF$_2$—, —CF$_2$O—, —CH=CH—CH$_2$CH$_2$— or a single bond, m is 0, 1 or 2,
n is 0 or 1,
L$^1$, L$^2$, and L$^3$ are each, independently of one another, H or F, and Y is —C≡C—, —CH=CH—, —CF=CH—, —CH=CF— or —CF=CF—, with the provisos that, in the case where
(1) Y is —CH=CH—,
  a) n=1 and Z$^3$ is a single bond or
  b) L$^1$ and/or L$^2$ is/are fluorine or
  c) R is alkenyl or alkenyloxy having 2 to 12 carbon atoms or
  d) A$^2$ is a pyridine radical, a pyrimidine radical or a trans-1,4-cyclohexylene radical which is monosubstituted or disubstituted by fluorine or CH$_3$or
  e) one of the radicals Z$^1$, Z$^2$ or Z$^3$ is —CO—O—; and
(2) in the case where Y is —C≡C—
  a) A$^1$ or A$^2$ are each independently of one another
    a) a trans-1,4-cyclohexylene radical, in which one CH$_2$ group is replaced by —O—, or one or more non adjacent —CH$_2$— groups are replaced b, —S— or
    b) trans-1,4-cyclohexenylene or
    c) a radical from the group consisting of 1,4-bicyclo [2.2.2] octylene, piperidine-1,4-diyl, naphthalene-2,6-diyl, decahydronaphthalene-2,6-diyl and 1,2,3,4-tetrahydronaphthalene-2, 6-diyl where the radicals (a) and (b) may be monosubstituted or disubstituted by fluorine or CH$_3$, or
  b) at least one of Z$^1$, Z$^2$ and Z$^3$ is —OCF$_2$— or —CF$_2$O—.

2. Compounds claim 1 characterized in that Y is —C≡C— or —CF=CF—.

3. Compounds claim 1 characterized in that R is alkenyl or alkenyloxy having 2 to 12 carbon atoms.

4. A liquid-crystalline medium having at least two liquid-crystalline components, characterized in that it comprises at least one compound according to claim 1.

5. Liquid-crystal display element, characterized in that it contains a liquid-crystalline medium according to claim 4.

6. In an electro-optical display element comprising, as dielectric, a liquid-crystalline medium, the improvement wherein said medium is in accordance with claim 4.

7. In a method of generating an electro-optical display using a liquid-crystal display element containing a liquid-crystal medium, the improvement wherein said medium is in accordance with claim 4.

8. An acetylene derivative of the formula I

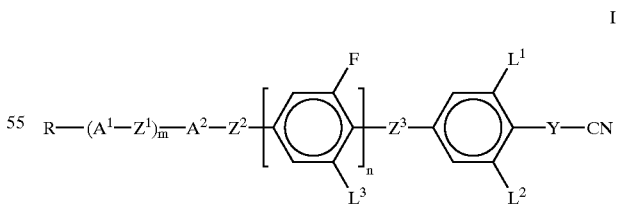

in which

R is an alkyl or alkenyl radical having 1 to 15 carbon atoms which is unsubstituted, monosubstituted by CN or CF$_3$ or at least monosubstituted by halogen, where, in addition, one or more —CH$_2$— groups in these radicals may be replaced, in each case independently of one another, by —O—, —S—,

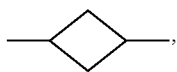

—CO—, —CO—O—, —O—O— or —O—CO—O— in such a way that O atoms are not linked directly to one another, $A^1$ and $A^2$ are each, independently of one another,
(a) a trans-1,4-cyclohexylene radical, in which, in addition, one or more nonadjacent —CH$_2$— groups may be replaced by —O— and/or —S—,
(b) a 1,4-phenylene radical, in which, in addition, one or two CH groups may be replaced by N,
(c) trans-1,4-cyclohexenylene,
(d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene, 2,6-diyl,
where the radicals (a) to (c) may be monosubstituted or disubstituted by fluorine or CH$_3$, $Z^1$, $Z^2$ and $Z^3$ are each, independently of one another, —CO—O—, —O—CO—, —CH$_2$O—, —OCH$_2$—, —CH$_2$CH$_2$—, —CH=CH—, —C≡C—, —(CH$_2$)$_4$—, —OCF$_2$—, —CF$_2$O—, —CH=CH—CH$_2$CH$_2$— or a single bond, m is 0, 1 or 2, n is 0 or 1, $L^1$, $L^2$, and $L^3$ are each, independently of one another, H or F, and Y is —CF=CH—, —CH=CF— or —CF=CF—.

9. An acetylene derivative of the formula I

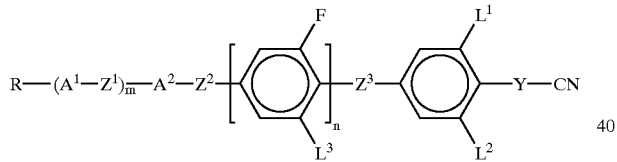

in which

R R is an alkyl or alkenyl radical having 1 to 15 carbon atoms which is unsubstituted, monosubstituted by CN or CF$_3$ or at least monosubstituted by halogen, where, in addition, one or more —CH$_2$— groups in these radicals may be replaced, in each case independently of one another, by —O—, —S—,

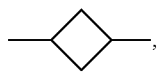

—CO—, —CO—O—, —O—O— or —O—CO—O— in such a way that O atoms are not linked directly to one another, $A^1$ and $A^2$ are each, independently of one another,
(a) a trans-1,4-cyclohexylene radical, in which, in addition, one or more nonadjacent —CH$_2$— groups may be replaced by —O— and/or —S—,
(b) a 1,4-phenylene radical, in which, in addition, one or two CH groups may be replaced by N,
(c) trans-1,4-cyclohexenylene,
(d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene, 2,6-diyl,
where the radicals (a) to (c) may be monosubstituted or disubstituted by fluorine or CH$_3$, $Z^1$, $Z^2$ and $Z^3$ are each, independently of one another, —CO—O—, —O—CO—, —CH$_2$O—, —OCH$_2$—, —CH$_2$CH$_2$—, —CH=CH—, —C≡C—, —(CH$_2$)$_4$—, —OCF$_2$—, —CF$_2$O—, —CH=CH—CH$_2$CH$_2$— or a single bond, wherein at least one of $Z^1$, $Z^2$ and $Z^3$ is —OCF$_2$— or —CF$_2$O—, m is 0, 1 or 2, n is 0 or 1, $L^1$, $L^2$, and $L^3$ are each, independently of one another, H or F, and Y is —C≡C—, —CH=CH—, —CF=CH—, —CH=CF— or —CF=CF—.

10. An acetylene derivative of the formula I

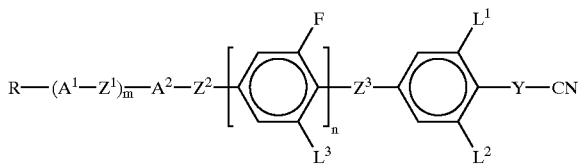

in which

R is an alkyl or alkenyl radical having 1 to 15 carbon atoms which is unsubstituted, monosubstituted by CN or CF$_3$ or at least monosubstituted by halogen, where, in addition, one or more —CH$_2$— groups in these radicals may be replaced, in each case independently of one another, by —O—, —S—,

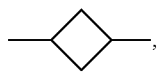

—CO—, —CO—O—, —O—O— or —O—CO—O— in such a way that O atoms are not linked directly to one another, $A^1$ and $A^2$ are each, independently of one another,
(a) a trans-1,4-cyclohexylene radical, in which, in addition, one or more nonadjacent —CH$_2$— groups may be replaced by —O— and/or —S—,
(b) a 1,4-phenylene radical, in which, in addition, one or two CH groups may be replaced by N,
(c) trans-i1,4-cyclohexenylene,
(d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene, 2,6-diyl,
where the radicals (a) to (c) may be monosubstituted or disubstituted by fluorine or CH$_3$, and wherein at least one of $A^1$ and $A^2$ is a radical (c) or (d), $Z^1$, $Z^2$ and $Z^3$ are each, independently of one another, —CO—O—, —O—CO—, —CH$_2$O—, —OCH$_2$—, —CH$_2$CH$_2$—, —CH=CH—, —C≡C—, —(CH$_2$)$_4$—, —OCF$_2$—, —CF$_2$O—, —CH=CH—CH$_2$CH$_2$— or a single bond, m is 0, 1 or 2, n is 0 or 1, $L^1$, $L^2$, and $L^3$ are each, independently of one another, H or F, and Y is —C≡C—, —CH=CH—, —CF=CH—, —CH=CF— or —CF=CF—, with the proviso that, in the case where
Y=—C≡C— or is —CH=CH—,
a) n=1 and $Z^3$ is a single bond or
b) $L^1$ and/or $L^2$ is/are fluorine or
c) R is alkenyl or alkenyloxy having 2 to 12 carbon atoms or
d) $A^2$ is a pyridine radical, a pyrimidine radical or a trans-1,4-cyclohexylene radical which is monosubstituted or disubstituted by fluorine or $CH_3$ or
e) one of the radicals $Z^1$, $Z^2$ or $Z^3$ is —CO—O—.

11. An acetylene derivative of the formula I

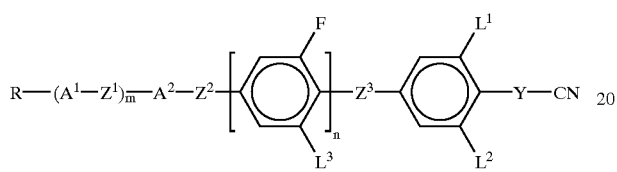

in which

R is an alkyl or alkenyl radical having 1 to 15 carbon atoms which is unsubstituted, monosubstituted by CN or $CF_3$ or at least monosubstituted by halogen, where, in addition, one or more —$CH_2$— groups in these radicals may be replaced, in each case independently of one another, by —O—, —S—,

—CO—, —CO—O—, —O—O— or —O—CO—O— in such a way that O atoms are not linked directly to one another, $A^1$ is, in each case, independently,
(a) a trans-1,4-cyclohexylene radical, in which, in addition, one or more nonadjacent —$CH_2$— groups may be replaced by —O— and/or —S—,
(b) a 1,4-phenylene radical, in which, in addition, one or two CH groups may be replaced by N,
(c) trans-1,4-cyclohexenylene,
(d) a radical from the group consisting of 1,4-bicyclo[2.2.2]octylene, piperidine-1,4-diyl, naphthalene-2,6-diyl, decahydronaphthalene-2,6-diyl and 1,2,3,4-tetrahydronaphthalene, 2,6-diyl,
where the radicals (a) to (c) may be monosubstituted or disubstituted by fluorine or $CH_3$, $A^2$ is trans-1,4-cyclohexenylene monosubstituted by F or is pyridine-2,5-diyl, $Z^1$, $Z^2$ and $Z^3$ are each, independently of one another, —CO—O—, —O—CO—, —$CH_2$O—, —$OCH_2$—, —$CH_2CH_2$—, —CH=CH—, —C≡C—, —$(CH_2)_4$—, —$OCF_2$—, —$CF_2O$—, —CH=CH—$CH_2CH_2$— or a single bond, m is 0, 1 or 2, n is 0 or 1, $L^1$, $L^2$, and $L^3$ are each, independently of one another, H or F, and Y is —C≡C—, —CH=CH—, —CF=CH—, —CH=CF— or —CF=CF—.

12. A compound of the formula I1

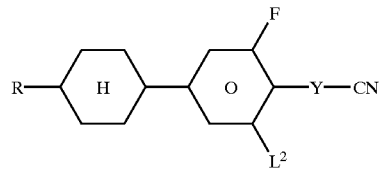

in which

R and $L^2$ are as defined in claim 1, and

Y is —CH=CH—, —CF=CH—, —CH=CF— or —CF=CF—.

13. A compound of the formula I2

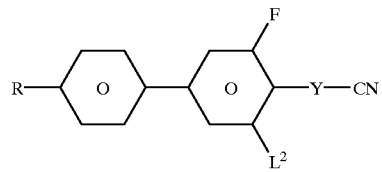

in which

R and $L^2$ are as defined in claim 1, and

Y is —CH=CH—, —CF=CH—, —CH=CF— or —CF=CF—.

14. A compound of the formula I3

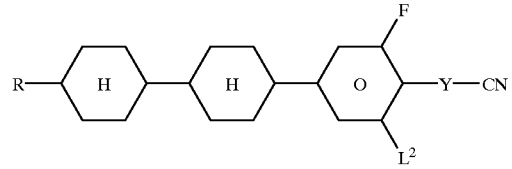

in which

R and $L^2$ are as defined in claim 1, and

Y is —CH=CH—, —CF=CH—, —CH=CF— or —CF=CF—.

15. A compound of the formula

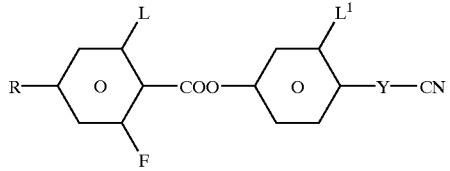

in which

L is H or F,

R and $L^1$ are as defined in claim 1, and

Y is —Ch=CH—, —CF=CH—, —CH=CF— or —CF=CF—.

16. A compound of the formula I16
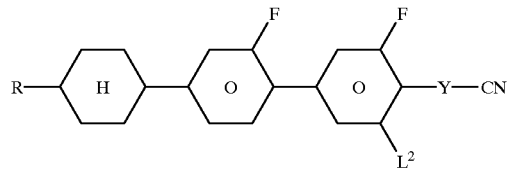
in which
R and $L^2$ are as defined in claim 1, and
Y is —CH=CH—, —CF=CH—, —CH=CF— or —CF=CF—.
* * * * *